(12) United States Patent
Huang

(10) Patent No.: US 7,756,712 B2
(45) Date of Patent: Jul. 13, 2010

(54) SIGNAL PROCESSING METHOD AND MODULE INVOLVING REARRANGING OF FREQUENCY DOMAIN DATA ON A VARIABLE AXIS

(76) Inventor: I-Shun Huang, No. 174, Hou-Ching-Chung St., Nan-Tzu Dist., Kaohsiung City (TW)

( * ) Notice: Subject to any disclaimer, the term of this patent is extended or adjusted under 35 U.S.C. 154(b) by 1501 days.

(21) Appl. No.: 10/947,804

(22) Filed: Sep. 22, 2004

(65) Prior Publication Data

US 2005/0228650 A1 Oct. 13, 2005

(30) Foreign Application Priority Data

Apr. 6, 2004 (TW) .............................. 93109511 A

(51) Int. Cl.
*G10L 19/00* (2006.01)
(52) U.S. Cl. ..................................... 704/500
(58) Field of Classification Search .................. 704/500
See application file for complete search history.

(56) References Cited

U.S. PATENT DOCUMENTS

| 4,928,251 | A | 5/1990 | Marzalek et al. ............ 364/484 |
| 6,480,820 | B1 | 11/2002 | Clopton et al. .............. 704/203 |
| 2002/0159425 | A1* | 10/2002 | Uesugi et al. ............... 370/342 |
| 2003/0086585 | A1* | 5/2003 | Rhoads ....................... 382/100 |

FOREIGN PATENT DOCUMENTS

| DE | 199 35 919 A | 2/2000 |
| WO | 98/02760 A1 | 1/1998 |

* cited by examiner

*Primary Examiner*—David R Hudspeth
*Assistant Examiner*—Jakieda R Jackson
(74) *Attorney, Agent, or Firm*—Ladas & Parry, LLP

(57) ABSTRACT

A signal processing method is provided for processing a plurality of input frequency domain data within a frequency band, each of the input frequency domain data having magnitude and phase characteristics and being associated with a phase parameter that corresponds to the phase characteristic thereof. The method includes: arranging the input frequency domain data in sequence on a variable axis; rearranging positions of the input frequency domain data on the variable axis with reference to at least the phase parameters of the input frequency domain data; and combining the rearranged input frequency domain data that are disposed on the same position on the variable axis to result in processed frequency domain data. The signal processing method can preserve and transmit phase characteristics at various frequencies, and is suitable for application to cochlear implant systems, retinal implant systems, and multi-phase data transmission systems.

34 Claims, 20 Drawing Sheets

SIGNAL PROCESSING METHOD AND MODULE INVOLVING REARRANGING OF FREQUENCY DOMAIN DATA ON A VARIABLE AXIS

CROSS-REFERENCE TO RELATED APPLICATION

This application claims priority of Taiwanese application no. 093109511, filed on Apr. 6, 2004.

BACKGROUND OF THE INVENTION

1. Field of the Invention

The invention relates to a signal processing method and module, more particularly to a signal processing method and module that can preserve phase characteristics of a signal to be processed thereby.

2. Description of the Related Art

A conventional digital signal processing method for processing audio and video signals usually adopts Hilbert Transform or Fast Fourier Transform (FFT) to transform data into magnitude and phase characteristics in the frequency domain. However, in cases where the phase characteristics of signals are not allowed to be transmitted, or when only specified phase characteristics of signals are transmitted, the original signal characteristics are not preserved during processing.

In the field of audio signal processing for cochlear implants, due to limitations to activation patterns of nerves and ganglion cells, current techniques only allow transmission of magnitude characteristics in the frequency domain and extraction of important voice features, such as transmission of fundamental frequencies and associated overtones, or finding of larger frequency domain signals ("Better speech recognition with cochlear implants", Wilson et al., Nature 352, p. 236-238, 1991; "Chimaeric sounds reveal dichotomies in auditory perception", Smith et al., Nature 416(6874), p. 87-90, 2002). In other words, phase characteristics, which are difficult to process, as well as noise and low-volume overtones, which are deemed to contain unimportant information to humans, are therefore discarded. Nevertheless, in order for the human central nervous system to recognize language contexts, musical melodies, sound sources, sound directions, etc., phase characteristics at various frequencies are factors that are too important to be neglected and are therefore required to be at best preserved during transmission.

The following are some methods relevant to the art of signal processing:

1) only those input frequency domain data that cross certain phases are transmitted:

In U.S. Pat. No. 6,480,820, there is disclosed a method of processing auditory data in which, after transformation of an audio signal into frequency domain data, those frequency domain data with no axis crossing are discarded. However, in practice, frequency domain data belonging to low frequencies (under 2000 Hz) and having no axis crossings actually form a large part of the audio signal. Hence, by discarding the frequency domain data having no axis crossings, most of the audio signal is actually lost. Moreover, in practical applications (especially in high frequency applications), it is possible that there may be no smooth axis crossings under certain analytical conditions. If interpolation is relied upon to generate frequency domain data with axis crossings for two frequency domain data with a large phase difference therebetween, distortion of the audio signal will result.

2) Traveling waves of basilar membrane response are simulated:

In U.S. Patent Publication No. 20030171786, acoustics signals are first transformed using FFT so as to obtain a plurality of data, each of which includes frequency magnitude and phase characteristics. Thereafter, by simulating the progress and delay phenomena of traveling waves, output signals are able to stimulate the cochlea at more accurate times. However, since imaginary data components are discarded during signal processing, phase characteristics and a part of magnitude characteristics are thus discarded. As a result, the original signal features are altered, making it impossible to reconstruct the original acoustic signal.

3) Simultaneous fast stimulation of electrodes:

In U.S. Pat. No. 6,504,525, there is disclosed a method of activating electrodes in a multi-channel electrode array of a cochlear implant using channel specific sampling sequences. However, in the disclosed method, the phase characteristics are also discarded during processing, which alters in part the features of the original audio signal.

Furthermore, in U.S. Pat. No. 6,647,297, in a typical method of signal processing in a retinal implant device, it is not allowed to transmit phase characteristics of spatial frequencies of an image signal. Since the phase characteristics are assumed to be equal, only magnitude characteristics of brightness or color stimulus are maintained.

Phase characteristics are critical to preserve the clarity of original audio and video signals ("The importance of phase in signals", Oppenheim et al., IEEE, Proceedings, vol. 69, p. 529-541, 1981). Therefore, if phase characteristics at various frequencies can be preserved and transmitted, the extent of recognizability of reconstructed audio and video signals will be dramatically improved.

Moreover, in orthogonal frequency division multiplexing (OFDM) modulation systems or other systems that require multi-phase data transmission, there is a need for a signal processing method in which original multi-phase signals are integrated into predefined phase angles so as to permit transmission of larger volumes of data.

SUMMARY OF THE INVENTION

Therefore, the object of the present invention is to provide a signal processing method and module that can preserve and transmit phase characteristics at various frequencies.

According to one aspect of the present invention, there is provided a signal processing method for processing a plurality of input frequency domain data within a frequency band, each of the input frequency domain data having magnitude and phase characteristics and being associated with a phase parameter that corresponds to the phase characteristic thereof. The signal processing method comprises the steps of:

a) arranging the input frequency domain data in sequence on a variable axis;

b) rearranging positions of the input frequency domain data on the variable axis with reference to at least the phase parameters of the input frequency domain data; and c) combining the rearranged input frequency domain data that are disposed on the same position on the variable axis to result in a plurality of processed frequency domain data.

According to another aspect of the present invention, there is provided a signal processing method for processing a signal that contains input frequency domain data, each of which is within one of a set of frequency bands having distinct frequency ranges. Each of the input frequency domain data has magnitude and phase characteristics. The signal processing method comprises the steps of:

a) arranging the input frequency domain data within a same one of the frequency bands in sequence on a variable axis; and b) rearranging positions of the input frequency domain data on the variable axis with reference to a frequency parameter that corresponds to a frequency characteristic of the same one of the frequency bands.

According to yet another aspect of the present invention, there is provided a signal processing module for processing a plurality of input frequency domain data within a frequency band, each of the input frequency domain data having magnitude and phase characteristics and being associated with a phase parameter that corresponds to the phase characteristic thereof. The signal processing module comprises a transforming unit, a sequence processing unit, and a combining unit. The transforming unit arranges the input frequency domain data in sequence on a variable axis. The sequence processing unit is coupled to the transforming unit, and rearranges positions of the input frequency domain data on the variable axis with reference to at least the phase parameters of the input frequency domain data. The combining unit is coupled to the sequence processing unit, and combines the rearranged input frequency domain data that are disposed on the same position on the variable axis to result in a plurality of processed frequency domain data.

The variable axis suitable in the present invention may be a time axis, a spatial axis or a visual angle axis.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1A:
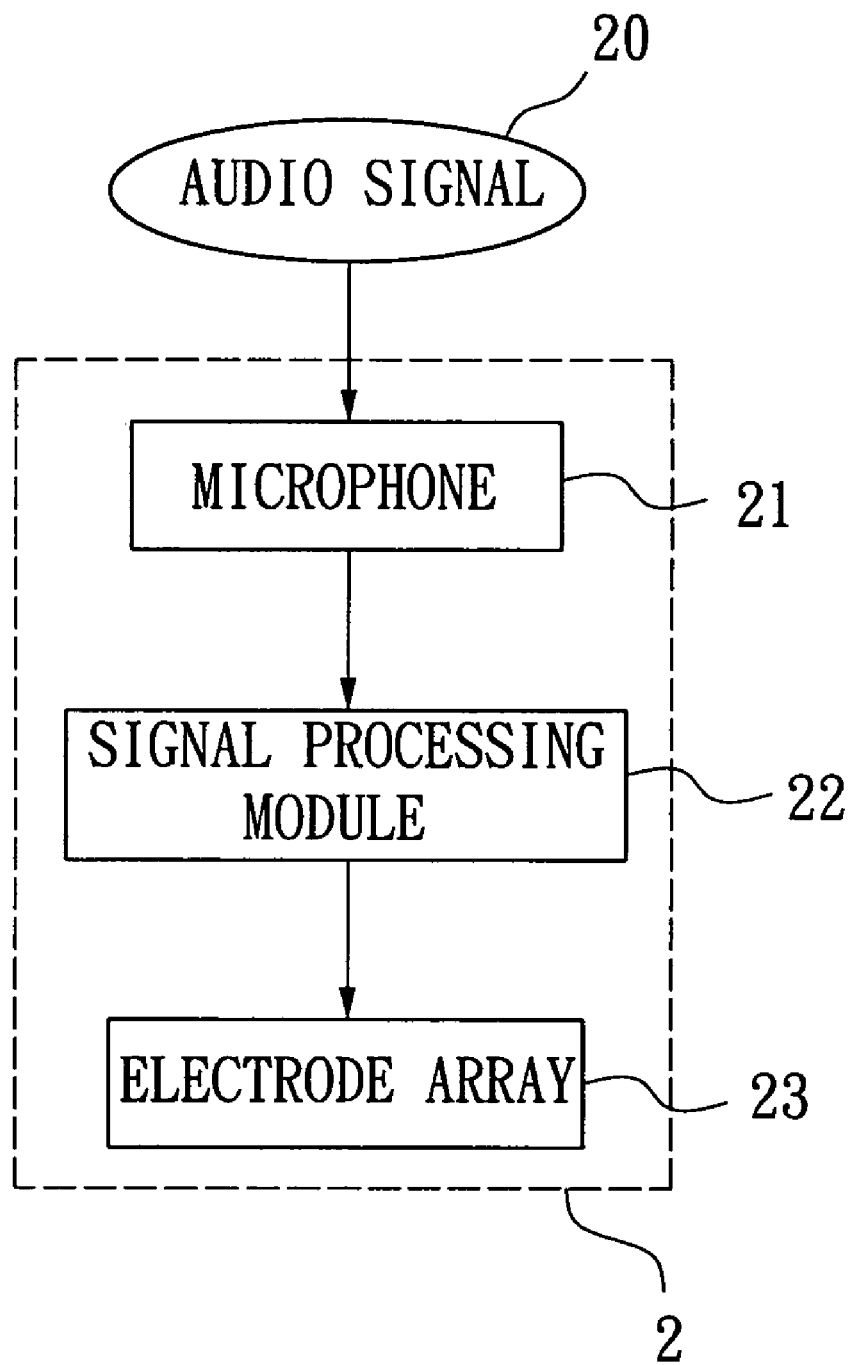
FIG. 1A is a simplified block diagram of a cochlear implant system that employs the first preferred embodiment of a signal processing method according to this invention.

Referring to FIG. 1A, a cochlear implant system 2 that employs the first preferred embodiment of a signal processing method according to the present invention is shown to include a microphone 21 for picking up an audio signal 20, a signal processing module 22 coupled to the microphone 21 for processing the audio signal 20, and an electrode array 23 coupled to the signal processing module 22 and adapted to stimulate the cochlea. In particular, the audio signal 20 is converted into electrical waves that stimulate the cochlea via the electrode array 23 such that the electrical waves are transmitted to the brain through the auditory nerves in order for a patient who is totally deaf to recover his hearing ability. It should be noted herein that the implanting region of the electrode array 23 is not limited to the cochlea. As a matter of fact, areas of auditory nerves, brainstem or auditory cortex of the brain are other candidates for implanting.

In this embodiment, the electrode array 23 includes twenty-two channel electrodes, each of which is implanted into a specific position of the cochlea and is associated with a corresponding specific frequency range. For instance, the electrode that is implanted at the base of the cochlea can receive the highest frequency range of an audio signal, and is thus associated with a first channel. On the other hand, the electrode that is implanted at the apex of the cochlea can receive the lowest frequency range of an audio signal, and is thus associated with a twenty-second channel. According to Greenwood's formula, a logarithmic relation exists between distances relative to the apex of the cochlea and the received frequencies. Assuming that the lower limit of the twenty-second channel is 125 Hz, and the upper limit of the first channel is 8000 Hz, the center frequencies of the twenty-second channel to the first channel are 147, 196, 253, 320, 397, 488, 594, 718, 863, 1031, 1229, 1459, 1727, 2040, 2406, 2834, 3332, 3914, 4594, 5387, 6313 and 7394 Hz, respectively.

Figure 1B:
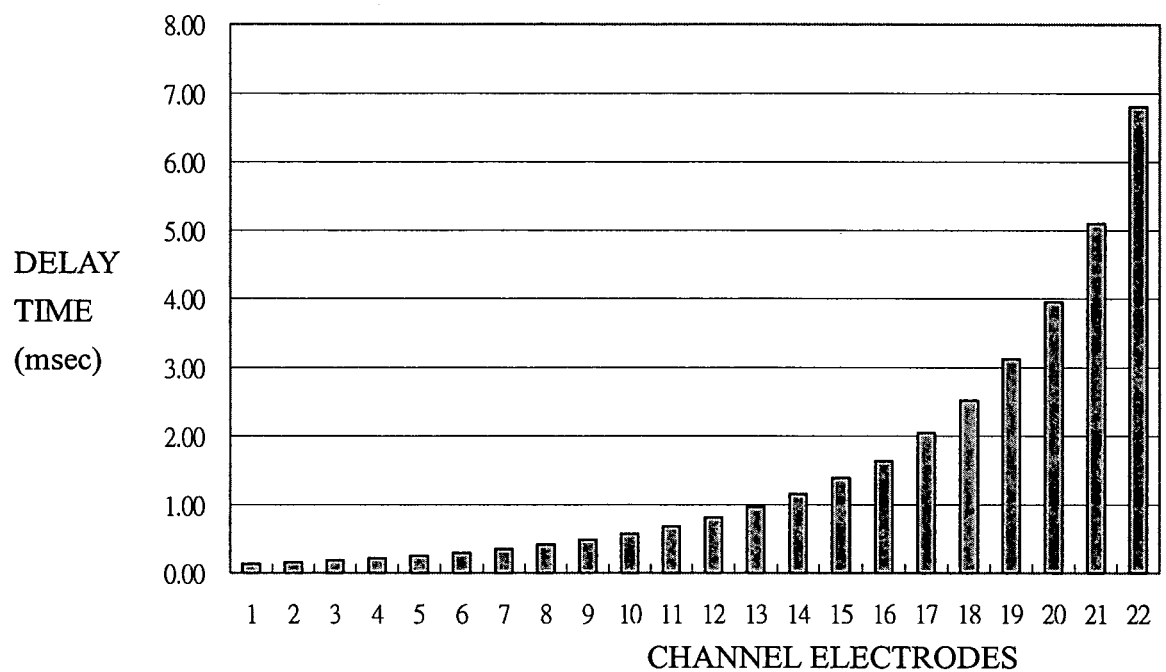
FIG. 1B is a graph illustrating delay times of traveling waves of basilar membrane that correspond to twenty-two channel electrodes.

Upon receipt by the human cochlea, an audio signal is transmitted from oval window (corresponding to the first channel electrode) to the apex of the cochlea (corresponding to the twenty-second channel electrode) in a form of traveling waves. Typical delay times of traveling waves of basilar membrane that correspond to the twenty-two channel electrodes are shown in FIG. 1B. Therefore, the signal processing method for the cochlear implant device should preferably be able to simulate the transmission of traveling waves. The following description illustrates how transmission of traveling waves is simulated in the present invention.

Figure 2:
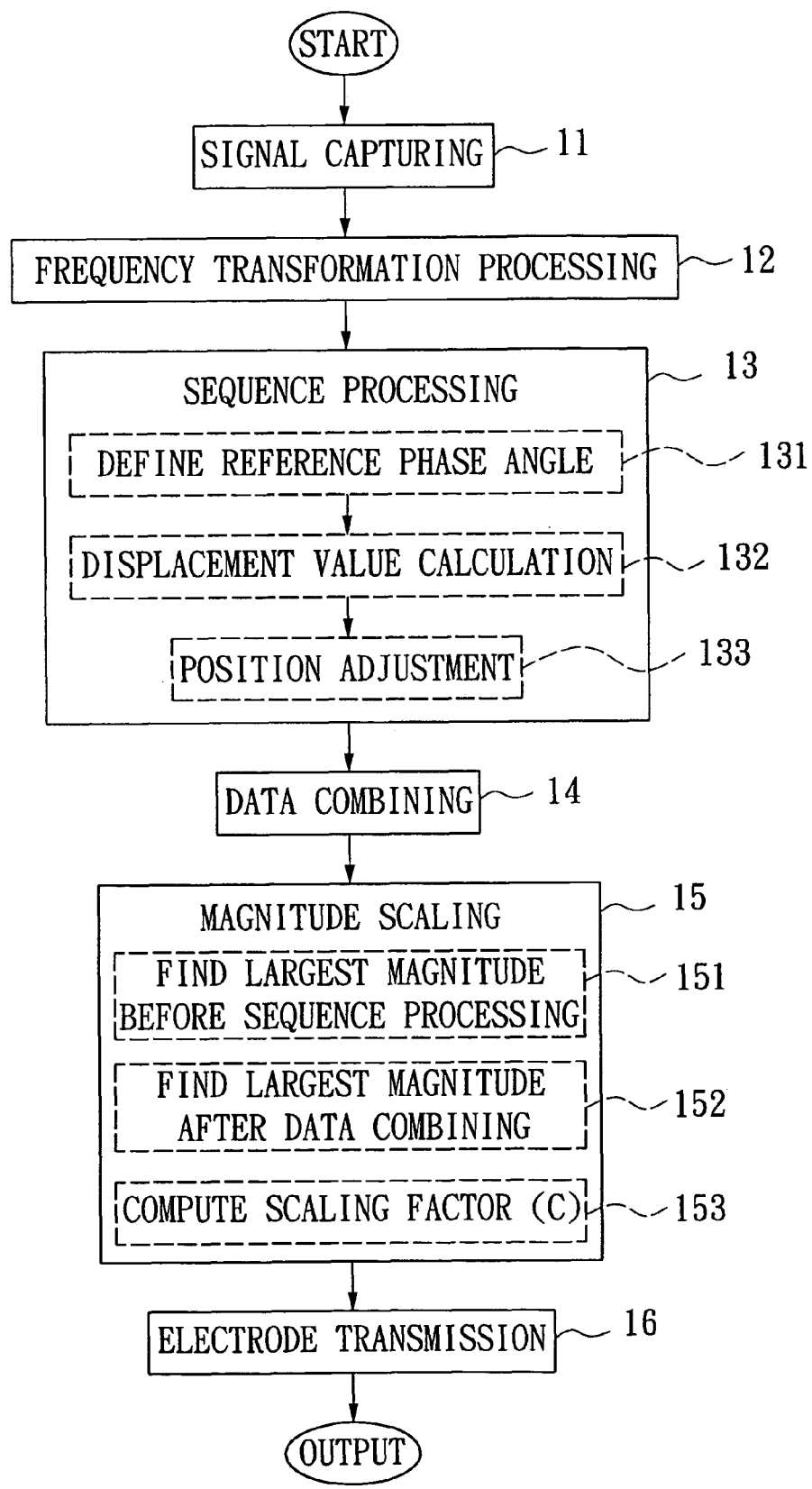
FIG. 2 is a flowchart to illustrate consecutive steps of the first preferred embodiment of the signal processing method of this invention.

Referring to FIG. 2, the first preferred embodiment of a signal processing method according to the present invention is shown to comprise the following steps:

Step 11—Signal Capturing

Figure 3A:
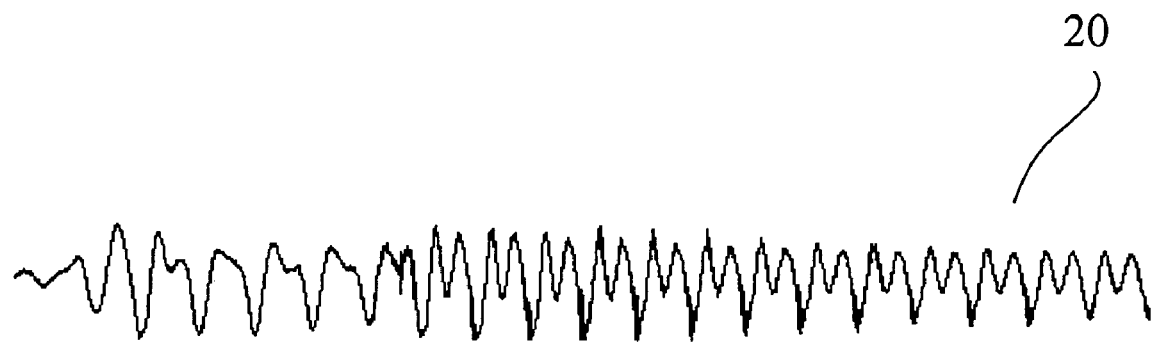
FIG. 3A illustrates an input audio signal to be processed using the signal processing method of the first preferred embodiment.

Referring to FIG. 3A, in this step, an analog audio stream 20 picked up by the microphone 21 is converted into a digital audio signal by the signal processing module 22 by sampling at a frequency that is more than twice the frequency of interest: Since frequencies important to human daily living environments generally range between 125 and 8000 Hz, 22050 Hz is chosen as the sampling frequency in this embodiment. However, it should be noted that the frequency range to be processed and the sampling frequency are not limited to those of the disclosed preferred embodiment.

Step 12—Frequency Transformation Processing

In this embodiment, the audio signal of FIG. 3A undergoes frequency transformation processing using Fast Fourier Transform (FFT) with 256 samples. In practice, other frequency transformation techniques, such as Butterworth filtering, Hilbert transformation, etc., may be applied.

In this embodiment, since each signal sampling point undergoes one-dimensional FFT, 22,050 frequency spectra are generated per second. In other words, 256 input frequency domain data are outputted per $\frac{1}{22050}$ second. Each input frequency domain data is expressed as a complex number $R(f, t)+I(f,t)i$, and is thus deemed to be a vector that contains magnitude and phase information of the input audio signal 20 at a particular frequency. The parameter (f) is a representative frequency of the input frequency domain data, whereas the parameter (t) is the position of the input frequency domain data on a variable axis, which is a time axis in this embodiment.

Figure 4A:
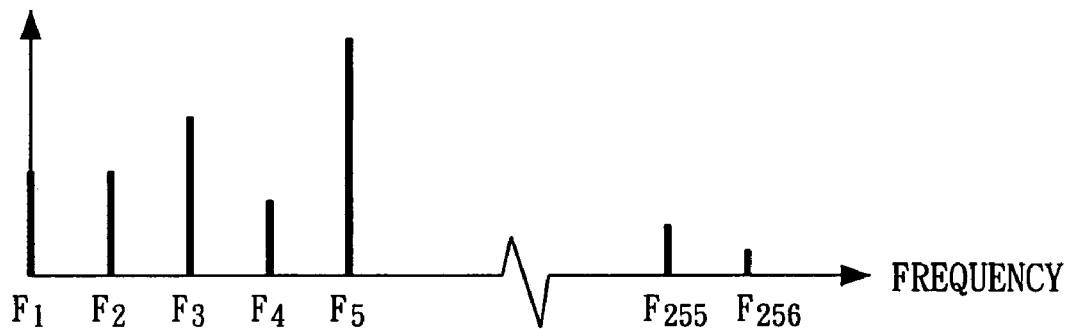
FIG. 4A illustrates magnitude characteristics of frequency domain data for a sampling point and obtained through Fast Fourier Transformation.
Figure 4B:
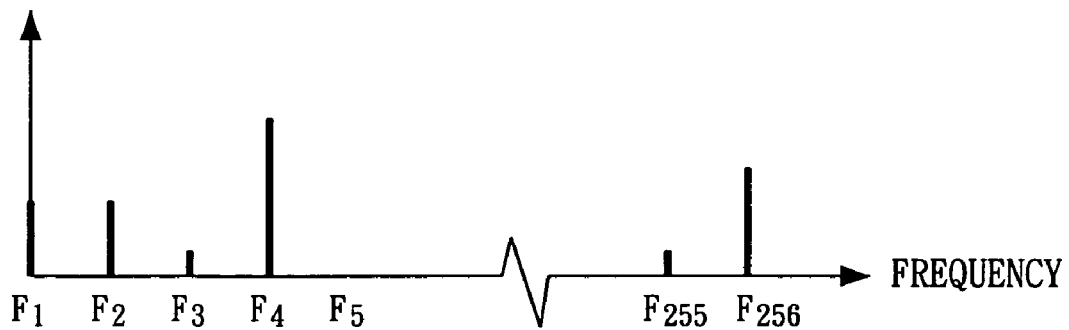
FIG. 4B illustrates phase characteristics of frequency domain data for a sampling point and obtained through Fast Fourier Transformation.

FIG. 4A illustrates magnitudes of 256 frequency components arranged on a frequency axis. The graph of FIG. 4A is a magnitude distribution of the input audio signal 20 on the frequency axis after the input audio signal 20 undergoes one-dimensional FFT. The 256 frequency components are arranged in an increasing order of frequency on the frequency axis, and each frequency component is within a frequency band that is represented by a linear center frequency ($F_1$-$F_{256}$) of the frequency band. The frequency range encompassed by all of the available frequency bands ranges from 125 to 8000 Hz. In the frequency vs. magnitude distribution of the input audio signal 20 shown in FIG. 4A, the magnitude at each frequency point is equal to the vector length, i.e., $(R^2+I^2)$. FIG. 4B is a graph of frequency vs. phase of the input audio signal 20 after the latter undergoes one-dimensional FFT, wherein the phase value at each frequency point is equal to $\tan^{-1}(I/R)$.

Figure 5A:
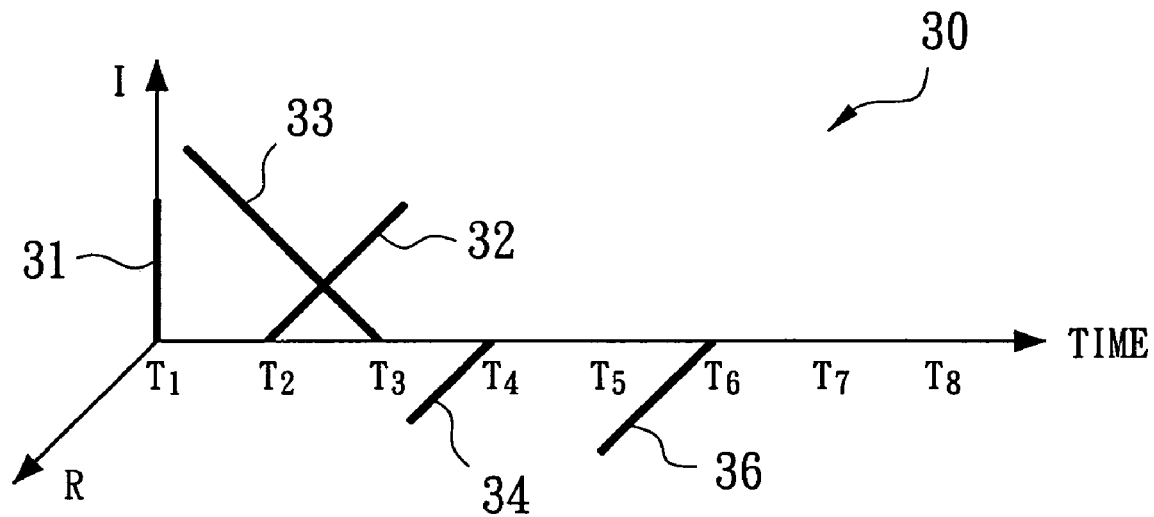
FIG. 5A illustrates distribution of frequency domain data within a first frequency band on a time axis.
Figure 5B:
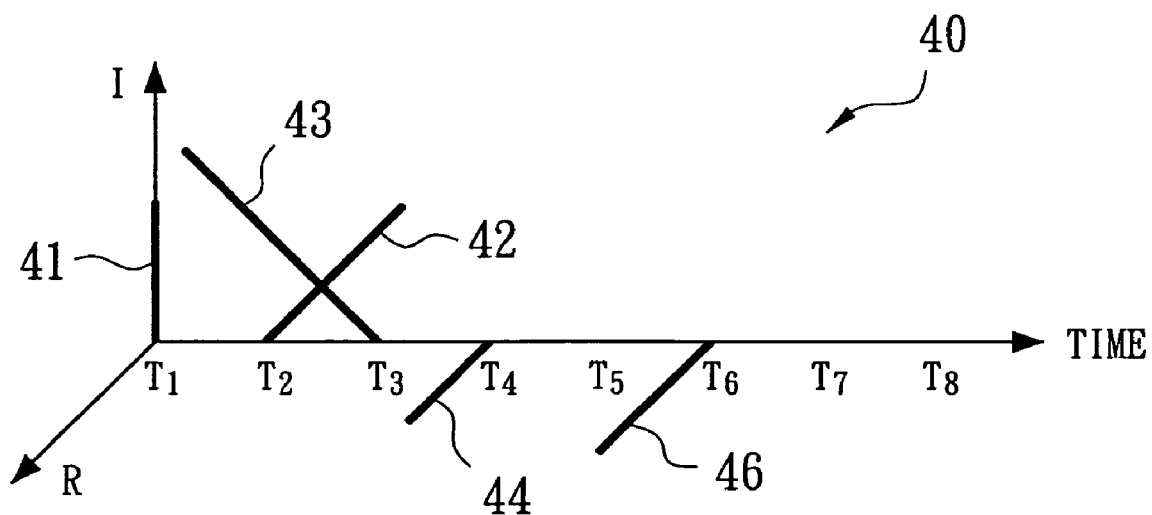
FIG. 5B illustrates distribution of frequency domain data within a second frequency band on a time axis.

In FIGS. 5A and 5B, for convenience of illustration, input frequency domain data of a specific frequency band and obtained using FFT for a plurality of sampling points are arranged in sequence on a time axis. In this embodiment, the unit distance of the time axis: $|T_1|=|T_2-T_1|=|T_3-T_2|=\ldots=1/22{,}050$ second. In addition, there are a real number axis (R) and an imaginary number axis (I) perpendicular to the time axis. When the input frequency domain data are generated using Butterworth Filtering or Hilbert Transformation, the R-axis and the I-axis are deemed to be coordinate axes for the magnitude and phase of the input frequency domain data.

FIG. 5A illustrates input frequency domain data 31-34 and 36 obtained using FFT for a first frequency band having a center frequency ($F_1$) at five sampling points ($T_1$-$T_4$ and $T_6$). The input frequency domain data 31-34 and 36 form a first data set 30, are arranged in sequence on the time axis, and indicate changes of the audio signal within the first frequency band with respect to time. The vector length of the input frequency domain data 31 at the sampling point ($T_1$) corresponds to the magnitude of the frequency ($F_1$) in FIG. 4A, whereas the phase angle of the input frequency domain data 31 at the sampling point ($T_1$) corresponds to the phase of the frequency ($F_1$) in FIG. 4B. In the same token, the input frequency domain data 32, 33, 34, 36 represent the magnitudes and phases of the frequency ($F_1$) at the respective sampling points ($T_2$, $T_3$, $T_4$, $T_6$).

FIG. 5B illustrates input frequency domain data 41-44 and 46 obtained using FFT for a second frequency band having a center frequency ($F_2$) at five sampling points ($T_1$-$T_4$ and $T_6$).

The input frequency domain data 41-44 and 46 form a second data set 40, are arranged in sequence on the time axis, and indicate changes of the audio signal within the second frequency band with respect to time. For convenience of illustration, the first and second data sets 30, 40 are shown to have the same distribution, which seldom occurs in actual practice. The vector length of the input frequency domain data 41 at the sampling point ($T_1$) corresponds to the magnitude of the frequency ($F_2$) in FIG. 4A, whereas the phase angle of the input frequency domain data 41 at the sampling point ($T_1$) corresponds to the phase of the frequency ($F_2$) in FIG. 4B. In the same token, the input frequency domain data 42, 43, 44, 46 represent the magnitudes and phases of the frequency ($F_2$) at the respective sampling points ($T_2$, $T_3$, $T_4$, $T_6$).

Third to $256^{th}$ data sets for third to $256^{th}$ frequency bands are obtained in the manner described above. Each of the frequency bands falls within one of the aforesaid twenty-two channels, such that each of the channels includes at least one of the frequency bands.

Step 13—Sequence Processing

With reference to FIGS. 5A, 5B, 6A and 6B, in the present embodiment, phase information is preserved and is not discarded during signal processing so that important features of the audio input signal 20 are not lost and so that errors can be reduced to a minimum. Therefore, in step 13, by calculating the time required for phase change at a specific frequency, the positions of the input frequency domain data for a frequency band on the time axis can be rearranged so as to result in a uniform phase angle by introducing appropriate displacement values to result in a position-adjusted sequence on the time axis in order to realize the objective of compression and complete transmission.

It is worth noting that, in the following processing steps of the preferred embodiment, only those input frequency domain data having frequencies and magnitudes within the human audible range are subjected to sequence processing. There is no need to perform sequence processing for high frequency or low decibel signals outside the scope of the human audible range. Certainly, it is feasible to introduce a filtering operation in step 12 such that only those input frequency domain data that have frequencies and magnitudes falling within the range of interest are present on the time axis.

Step 13 includes the following sub-steps:

Sub-step 131—Defining a reference phase angle ($\theta_0$)

The reference phase angle ($\theta_0$) is an arbitrary angle. In this preferred embodiment, the reference phase angle ($\theta_0$) is 0 for illustrative purposes.

Sub-step 132—Displacement Value Calculation

Taking the input frequency domain data 31 at the sampling point ($T_1$) as an example, the minimum displacement value ($\Delta T$) on the time axis for the input frequency domain data 31 may be obtained from the following Formula 1:

$$\Delta T = (\Delta\theta/2\pi) \times T \quad \text{Formula 1}$$

wherein (T) is a frequency parameter for the first data set 30 and is equal to $1/F_1$, and ($\Delta\theta$) is a phase difference between the input frequency domain data 31 and the reference phase angle ($\theta_0$) and is equal to $\pi/2$. For convenience of illustration, it is assumed herein that $T=12|T_1|$. Hence, for the input frequency domain data 31, $\Delta T=3|T_1|$, which indicates that the position of the input frequency domain data 31 is to be rearranged for output at the sampling point ($T_4$).

Note that if two reference phase angles, such as 0 and $\pi$, are defined in step 131, the phase difference ($\Delta\theta$) is then equal to the smaller difference between the original phase of the input frequency domain data and a respective one of the reference phase angles 0 and $\pi$ in a specified direction, i.e., the counterclockwise or clockwise direction.

Sub-Step 133—Position Adjustment

Figure 6A:
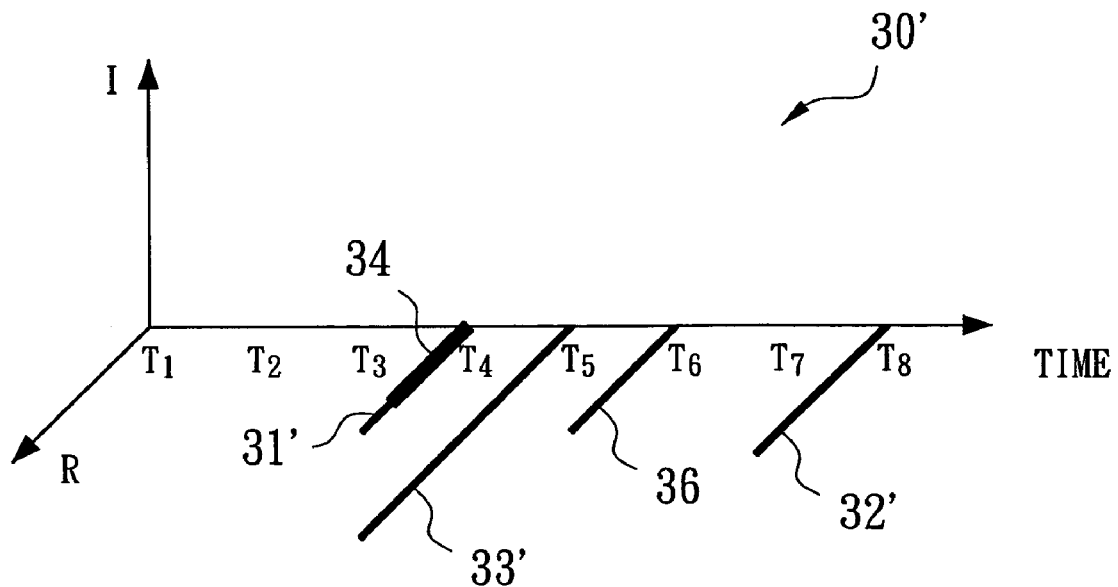
FIG. 6A illustrates distribution of the frequency domain data within the first frequency band on the time axis after sequence processing according to the signal processing method of the first preferred embodiment.

In this preferred embodiment, after moving the input frequency domain data 31, 32, 33 of FIG. 5A from initial positions on the time axis to adjusted positions on the time axis with reference to the displacement values ($\Delta T$) calculated in step 132, as best shown in FIG. 6A, the phase characteristics of the rearranged input frequency domain data 31', 32', 33' are set to correspond to the reference phase angle (i.e., 0), thereby resulting in the sequence-processed first data set 30' of FIG. 6A.

In other words, through Formula 1, the input frequency domain data 31, 32, 33 in FIG. 5A are moved from the initial sampling points ($T_1$), ($T_2$), ($T_3$) on the time axis to adjusted output points ($T_4$), ($T_8$), ($T_5$) on the time axis, as shown in FIG. 6A, such that the phase angles of the rearranged input frequency domain data 31', 32', 33' of the sequence-processed first data set 30' can be all set to correspond to the reference phase angle (i.e., 0). The input frequency domain data 34, 36 whose phase angles are originally 0 (i.e., $\Delta\theta=0$), and those input frequency domain data whose magnitudes are negligible (such as the initial data present at sampling point $T_5$) need not undergo sequence processing.

Figure 6B:
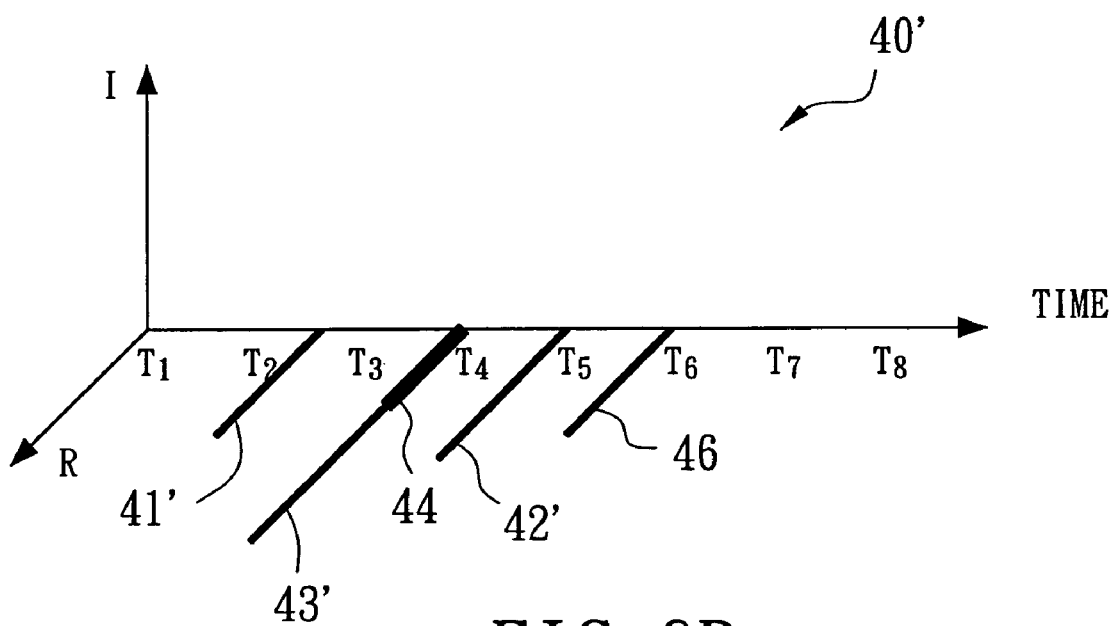
FIG. 6B illustrates distribution of the frequency domain data within the second frequency band on the time axis after sequence processing according to the signal processing method of the first preferred embodiment.

Through the aforementioned sub-steps 131-133, the input frequency domain data 41-44 and 46 of the second data set 40 shown in FIG. 5B can be rearranged using Formula 1 to result in the sequence-processed second data set 40' of FIG. 6B, in which the phase angles of the rearranged input frequency domain data 41', 42', 43' of the sequence-processed second data set 40' are all set to correspond to the reference phase angle (i.e., 0). In this preferred embodiment, for simplicity of illustration, it is assumed that $F_2=2F_1$, such that the frequency parameter (T) for the second data set 40 is equal to $6|T_1|$. As a result, although the magnitude and phase characteristic of the input frequency domain data of the second data set 40 are the same as those of the first data set 30, the calculated displacement values ($\Delta T$) will be different. Therefore, the positions of the rearranged input frequency domain data 41', 42', 43' in the sequence-processed second data set 40' on the time axis will be different from those of the sequence-processed first data set 30'. As evident from FIG. 6B, the input frequency domain data 41, 42, 43 shown in FIG. 5B are moved from the initial sampling points ($T_1$), ($T_2$), ($T_3$) on the time axis to adjusted output points, i.e., midway between ($T_2$) and ($T_3$), ($T_5$), and ($T_4$), on the time axis.

Likewise, the input frequency domain data 44, 46 whose phase angles are originally 0 (i.e., $\Delta\theta=0$), and those input frequency domain data whose magnitudes are negligible (such as the initial data present at sampling point $T_5$) need not undergo sequence processing.

Using the same procedure, the input frequency domain data for the third to the $256^{th}$ frequency bands are adjusted so that the phase characteristics of all of the input frequency domain data correspond to the reference phase angle (i.e., 0).

It should be noted herein that, due to hardware restrictions, such as output signals are generated only at fixed time intervals, or simultaneous output of signals is not permitted, etc., the actual output point may be chosen to be the nearest practical output point instead of the theoretical output point.

In the aforesaid Formula 1, the displacement value ($\Delta T$) is calculated as a function of the phase difference ($\Delta\theta$) and the frequency parameter (T) for the specified frequency band. In the following alternative embodiments, while the displacement value ($\Delta T$) is calculated as a function of only one of the aforesaid parameters, the resulting effects are still better than those attained in the prior art.

1) First modification: The parameter (T) is variable, whereas the parameter (Δθ) is fixed.

Figure 7:
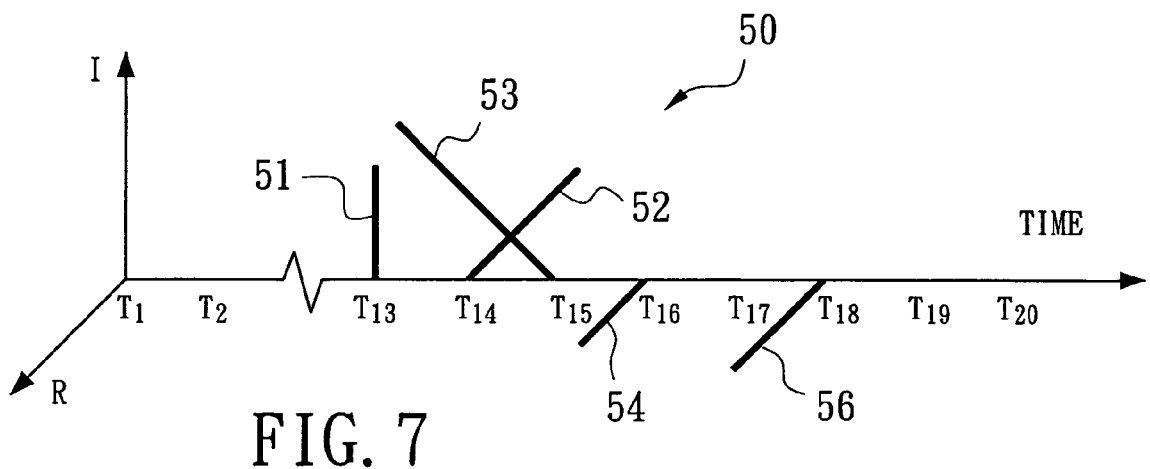
FIG. 7 illustrates distribution of the frequency domain data within the first frequency band on the time axis after sequence processing according to a first modification of the first preferred embodiment.

In the first modification, it is assumed that the phase difference (Δθ) for all of the input frequency domain data is $2n$. Thus, for the first data set 30 of FIG. 5A, since $T=1/F_1$, if the phase characteristics of the input frequency domain data 31-34 and 36 are to remain unchanged, the input frequency domain data 31-34 and 36 will be delayed by $T=12|T_1|$. The resulting sequence-processed first data set 50 is shown in FIG. 7 to include input frequency domain data 51-54 and 56 outputted at sampling points $(T_{13}-T_{16}$ and $T_{18})$, respectively. In the same manner, the input frequency domain data of all other frequency bands are adjusted according to the frequency characteristics of the respective frequency band.

When the sequence-processed data sets thus obtained are further processed in the manner to be described hereinafter before subsequent output to the electrode array, the delay states of transmission of traveling waves through the basilar membrane of the human cochlear as shown in FIG. 1B are simulated accordingly.

2) Second modification: The parameter (Δθ) is variable, and a specified frequency is defined.

In the second modification, instead of using the frequency characteristics of each frequency band as a parameter in the calculation of the displacement value (ΔT), a specified frequency, such as the fundamental frequency (e.g., $F_5$) of the audio signal 20, is employed to set a fixed value for the frequency parameter (T) suitable for all frequency bands. In other words, the displacement value (ΔT) for the input frequency domain data of all frequency bands is calculated as $\Delta T=(\Delta\theta/2\pi)\times(1/F_5)$. That is, the displacement value (ΔT) depends only on the parameter (Δθ). However, it should be noted that, since the fundamental frequency of an audio signal is related to the source and is not fixed, the parameter (T) is not necessarily a constant.

Moreover, in order to reduce overall calculations in step 13, it is preferable to decompose the input frequency domain data into vector components before proceeding with the aforesaid sequence-adjustment processing operations. This will be described in greater detail in the following third modification.

3) Third modification: Sequence processing based on vector components.

The third modification of the first preferred embodiment differs from the original first preferred embodiment in that a vector decomposition sub-step is added between the sub-steps 131 and 132.

Figure 8A:
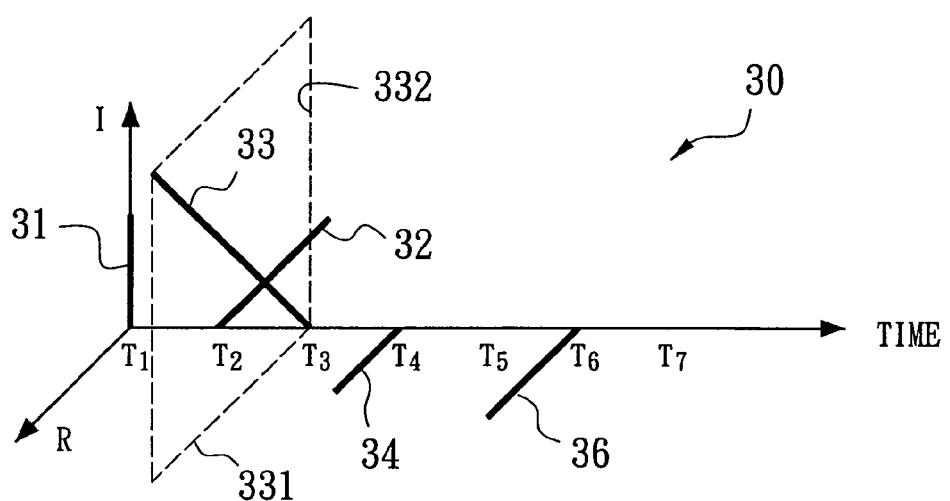
FIG. 8A illustrates how frequency domain data within the first frequency band can be decomposed according to a third modification of the first preferred embodiment.

Taking the input frequency domain data 33 at the sampling point $(T_3)$ of FIG. 5A as an example, the input frequency domain data 33 can be decomposed into a horizontal component 331 having a phase equal to the reference phase angle $(\theta_0)$, and a vertical component 332 perpendicular to the horizontal component 331, as best shown in FIG. 8A. The horizontal component 331 of the input frequency domain data 33 is not required to be moved from the sampling point $(T_3)$, whereas only the displacement value (ΔT) for the vertical component 332 is required to be calculated in step 132.

Figure 8B:
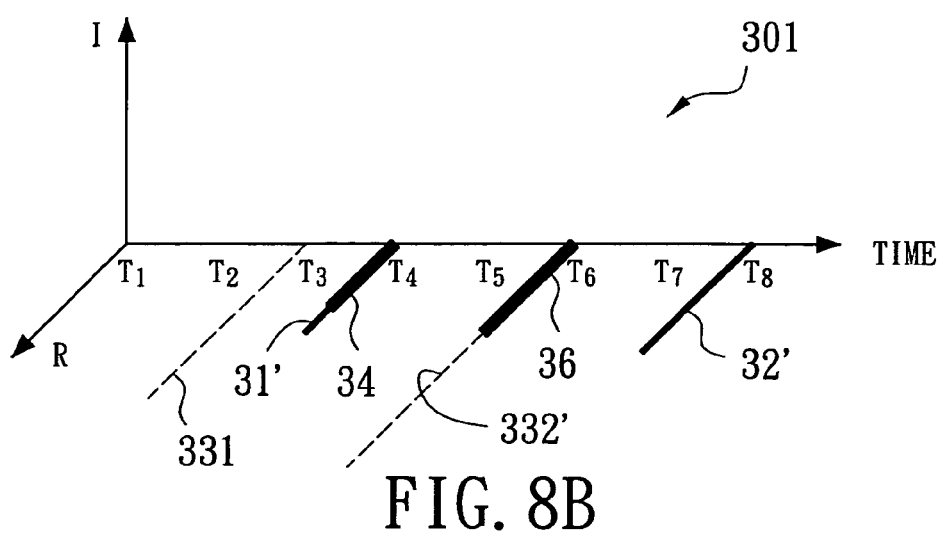
FIG. 8B illustrates distribution of the decomposed frequency domain data of FIG. 8A on the time axis after sequence processing according to the third modification of the first preferred embodiment.

In view of the foregoing, the parameter (Δθ) in Formula 1 can have one of the following four fixed values: 0 (such as the horizontal component 331 and the input frequency domain data 34, 36); $0.5\pi$ (such as the input frequency domain data 31 and the vertical component 332); $\pi$ (such as the input frequency domain data 32); and $1.5\pi$. As a result, there are only four displacement values (ΔT), namely 0, 0.25T, 0.5T and 0.75T, available for the decomposed vector components of all input frequency domain data of the first data set 30. A sequence-processed data set 301 corresponding to the first data set 30 is shown in FIG. 8B. When compared with FIG. 8A, the original vertical component 332 is moved to the sampling point $(T_6)$ to become the vertical component 332', and the input frequency domain data 31, 32 at the sampling points $(T_1), (T_2)$ are moved to the sampling points $(T_4), (T_8)$ to become the input frequency domain data 31', 32', respectively. The sequence-processed data sets for the second to the 256th frequency bands are obtained in the same manner.

Figure 9:
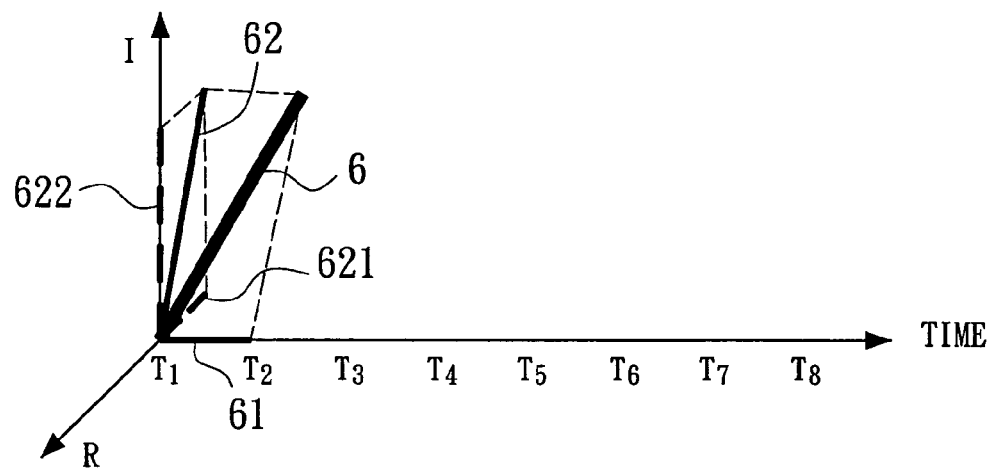
FIG. 9 illustrates frequency domain data having a component parallel to the time axis.

Moreover, the third modification of the first preferred embodiment is applicable to process those input frequency domain data having components parallel to the time axis. In the example of FIG. 9, the input frequency domain data 6 at the sampling point $(T_1)$ can be decomposed into a first component 61 parallel to the time axis and a second component 62 perpendicular to the time axis. The second component 62 can be further decomposed into a real number component 621 parallel to the R-axis, and an imaginary number component 622 parallel to the I-axis.

Figure 10A:
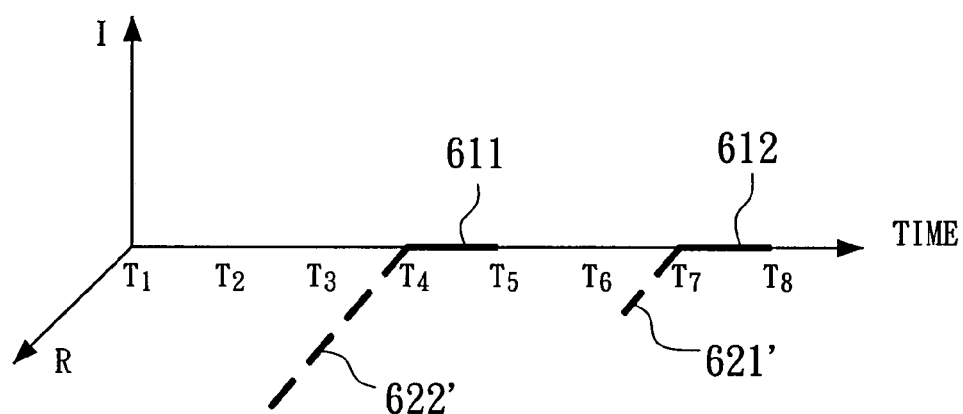
FIG. 10A illustrates how real and imaginary components of the frequency domain data of FIG. 9 are rearranged on the time axis according to the third modification of the first preferred embodiment, without taking into account the time-axis component.

Referring to FIG. 10A, the real number component 621 and the imaginary number component 622 of the second component 62 at the sampling point $(T_1)$ are adjusted in the above-described manner to result in a component 621' at the sampling point $(T_7)$ and a component 622' at the sampling point $(T_4)$. The component 61 at the sampling point $(T_1)$ is replaced by a corresponding component 611 at the sampling point $(T_7)$ and a corresponding component 612 at the sampling point $(T_4)$.

Figure 10B:
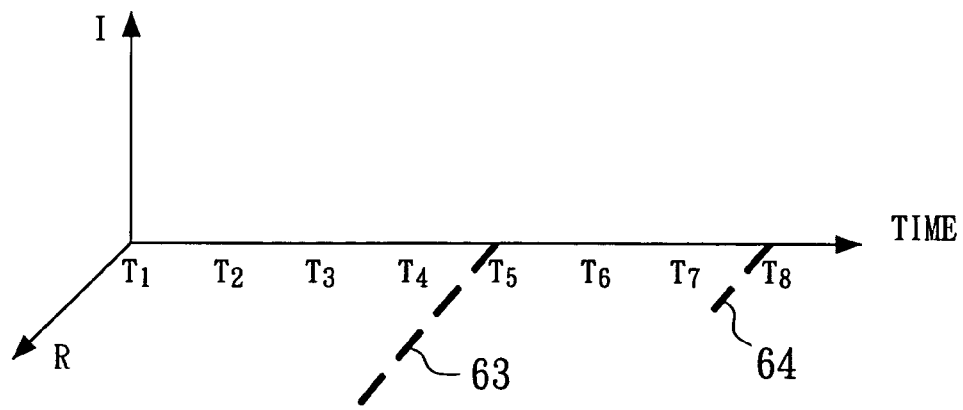
FIG. 10B illustrates how the real and imaginary components of the frequency domain data of FIG. 9 are rearranged on the time axis according to the third modification of the first preferred embodiment, after taking into account the time-axis component.

With further reference to FIG. 10B, since the components 611, 612 are parallel to the time axis, and thus indicate the rate of change of the components 621', 622' on the time axis, and since each of the components has a magnitude equal to $|T_1|$, the components 622', 621' are further displaced by $|T_1|$ so as to result in the components 63, 64 at the sampling points $(T_5), (T_8)$, respectively.

Figure 11A:
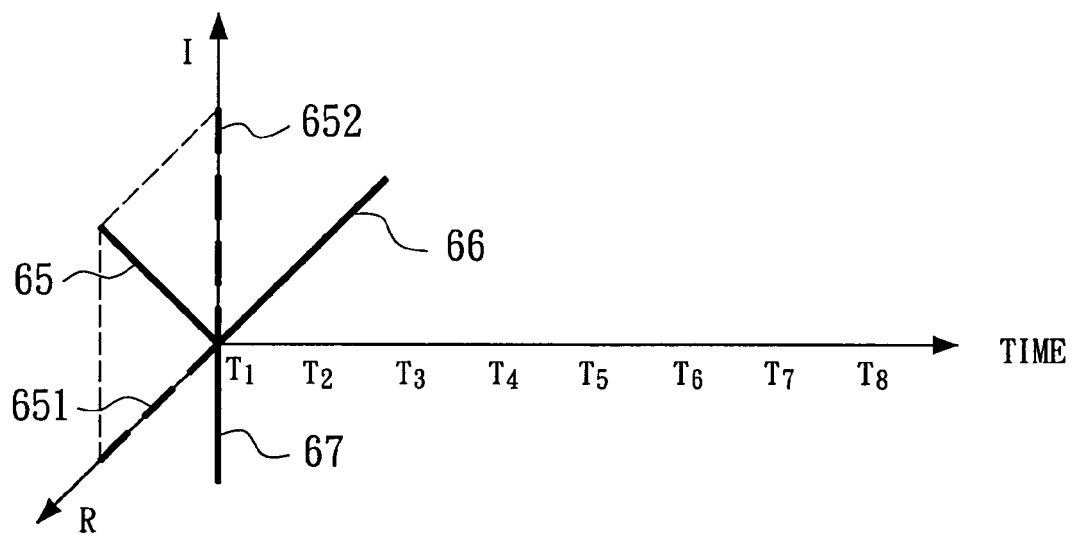
FIG. 11A illustrates a plurality of frequency domain data at a common sampling point.
Figure 11B:
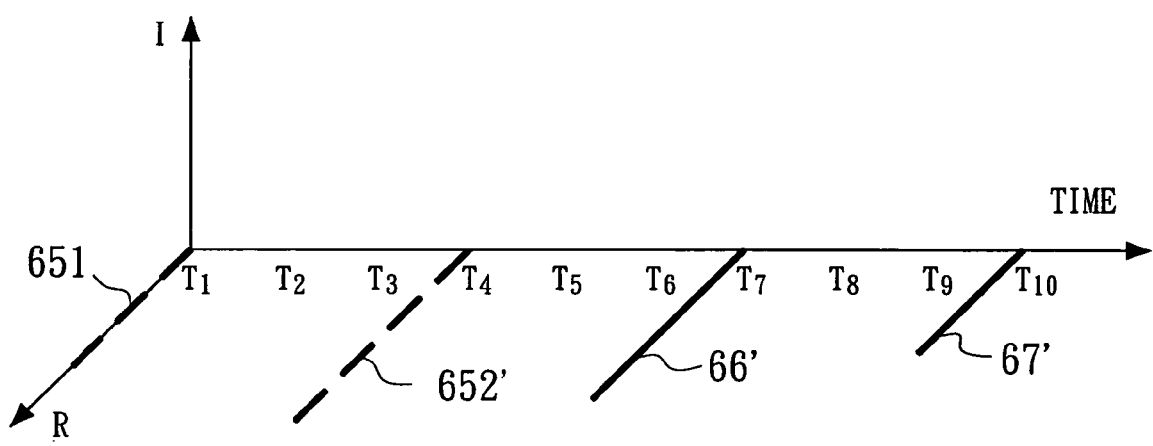
FIG. 11B illustrates distribution of the frequency domain data of FIG. 11A on the time axis after sequence processing according to the third modification of the first preferred embodiment.

Moreover, the processing method of this invention is suitable for processing a plurality of input frequency domain data that coexist at the same sampling point, as shown in FIG. 11A. Such a situation may arise as a result of vector decomposition of the original input frequency domain data. In FIG. 11A, the phase of the input frequency domain data 65 at the sampling point $(T_1)$ is $0.25\pi$, the phase of the input frequency domain data 66 at the sampling point $(T_1)$ is $\pi$, and the phase of the input frequency domain data 67 at the sampling point $(T_1)$ is $1.5\pi$. According to step 13 of the method of this embodiment, the input frequency domain data 65 may be displaced to midway between the sampling points $(T_2)$ and $(T_3)$. Alternatively, according to the third modification of the first preferred embodiment, the input frequency domain data 65 may be decomposed into a horizontal component 651 with a phase angle 0 and a vertical component 652 with a phase angle $0.5\pi$, whereas the input frequency domain data 66, 67 need not be decomposed. Thereafter, as shown in FIG. 11B, the vertical component 652 and the input frequency domain data 66, 67 are respectively adjusted to result in the input frequency domain data 652', 66', 67' at the sampling points $(T_4), (T_7), (T_{10})$, whereas the position of the horizontal component 651 at the sampling point $(T_1)$ is maintained.

From the foregoing, it is apparent that all input frequency domain data may be decomposed into vector components, which are subsequently subjected to position adjustment with reference to the displacement values (ΔT) calculated from at least one of the phase parameter (Δθ) and the frequency parameter (T).

Step 14—Data Combining

Figure 12A:
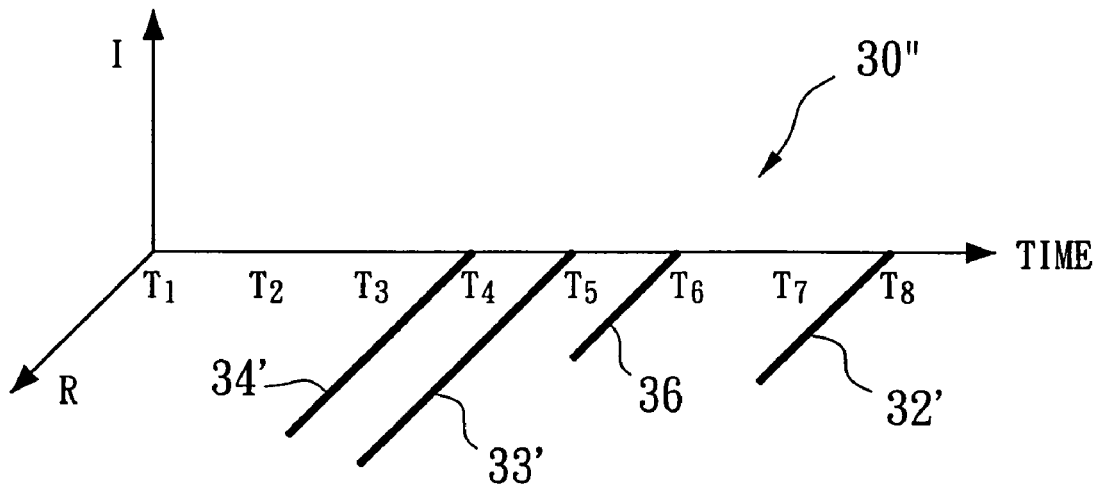
FIG. 12A illustrates distribution of the frequency domain data of the first frequency band on the time axis after rearranging and combining operations.
Figure 12B:
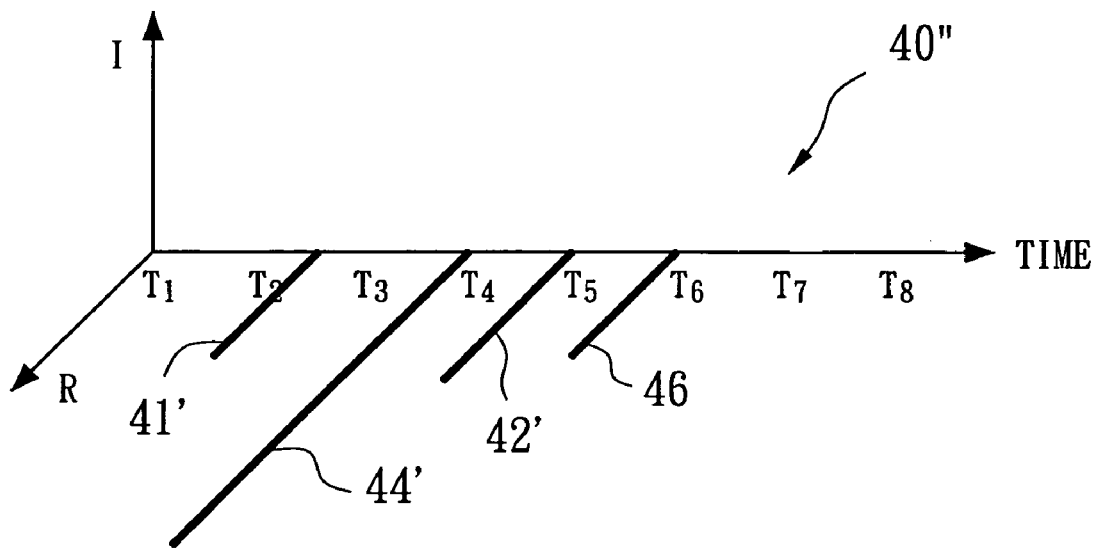
FIG. 12B illustrates distribution of the frequency domain data of the second frequency band on the time axis after rearranging and combining operations.

In this step, the sequence-processed data sets processed in step 13 are further processed by combining the rearranged input frequency domain data (i.e., summing the magnitudes of the rearranged input frequency domain data) that are disposed on the same position on the time axis, thereby resulting in the processed data sets 30", 40" of FIGS. 12A and 12B. If two or more reference phase angles were defined in step 131, the rearranged input frequency domain data are combined by vector summation.

For instance, since the input frequency domain data 31', 34 are present at the same sampling point ($T_4$) on the time axis in FIG. 6A, the magnitudes thereof are combined in step 14 so as to result in the processed frequency domain data 34' shown in FIG. 12A. In the same token, since the input frequency domain data 43', 44 are present at the same sampling point ($T_4$) on the time axis in FIG. 6B, the magnitudes thereof are combined in step 14 so as to result in the processed frequency domain data 44' shown in FIG. 12B.

In the same manner, when applied to the third modification of the first preferred embodiment, since the input frequency domain data 31', 34 and the input frequency domain data 36, 332' are present at the respective sampling points ($T_4$) and ($T_6$) on the time axis in FIG. 8B, they are likewise combined by magnitude summation in step 14.

Step 15—Magnitude Scaling

Figure 13:
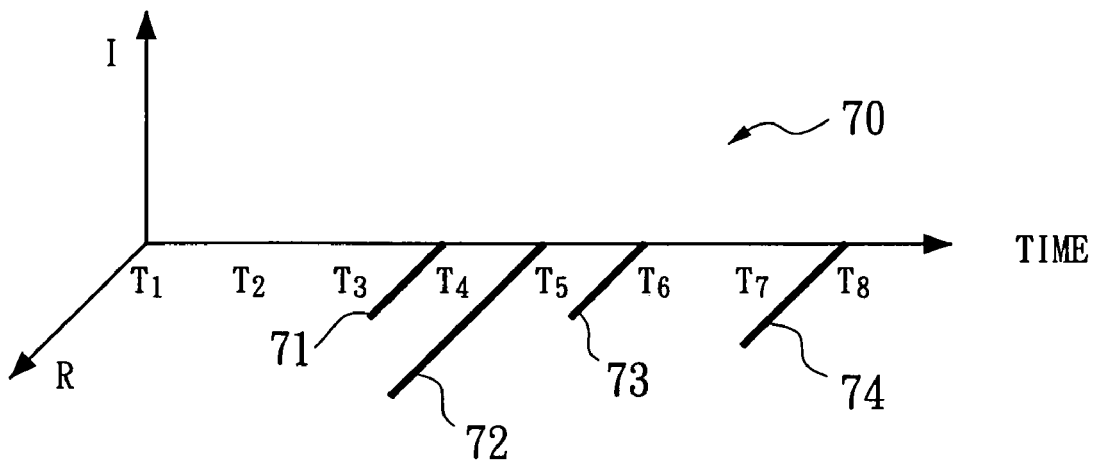
FIG. 13 illustrates distribution of the frequency domain data of FIG. 12A on the time axis after a magnitude scaling operation.

Referring to FIGS. 12A, 12B and 13, in view of the processing operations of steps 13 and 14, there is a tendency for the magnitudes of the processed frequency domain data to the right of the time axis (i.e., the sampling points are later) to have higher values. Therefore, the processed frequency domain data must be scaled by a scaling factor (C) so as to limit the magnitudes of the same to acceptable levels. Otherwise, the final output signal might be too strong and could cause injury to the patient or damage to instruments.

In this embodiment, the computation of the scaling factor (C) at a certain sampling point includes the following sub-steps:

Sub-step 151: First, the input frequency domain data with the largest magnitude among all frequency bands at a certain sampling point prior to sequence processing is determined. For example, it is assumed that the input frequency domain data 34 of the first data set 30 of FIG. 5A has the largest magnitude at the sampling point ($T_4$) prior to the sequence processing operation of step 13.

Sub-step 152: Next, the processed frequency domain data with the largest magnitude among all frequency bands at a certain sampling point after data combining is determined. For example, it is assumed that the processed frequency domain data 44' of the processed data set 40" of FIG. 12B has the largest magnitude at the sampling point ($T_4$) after the data combining operation of step 14.

Sub-step 153: Thereafter, the scaling factor ($C_4$) at the sampling point ($T_4$) is determined by dividing the largest magnitude found in sub-step 151 by the largest magnitude found in sub-step 152. Finally, the processed frequency domain data at the sampling point ($T_4$) for all frequency bands are then multiplied by the scaling factor ($C_4$).

The processed frequency domain data 34' in FIG. 12A will become the scaled frequency domain data 71 in FIG. 13 after scaling by the scaling factor ($C_4$). The processed frequency domain data 44' in FIG. 12B, which was determined in sub-step 152 to have the largest magnitude at the sampling point ($T_4$), will have its magnitude restored to a level comparable to that prior to the sequence processing operation of step 13 after being scaled by the scaling factor ($C_4$).

The scaled frequency domain data 72, 73, 74 at the sampling points ($T_5$), ($T_6$), ($T_8$) are obtained in a similar manner to result in the scaled data set 70 of FIG. 13. The scaled frequency domain data for all other frequency bands are obtained using essentially the same procedure set forth above.

The following are other feasible techniques for magnitude scaling that are applicable to the present invention:

1) The First Modification:

Unlike the embodiment described beforehand, instead of calculating the scaling factor from the largest values found in sub-steps 151 and 152, the scaling factor is calculated as the quotient of the magnitude of the input frequency domain data for a specific frequency band at a certain sampling point before the sequence processing operation of step 13 and the magnitude of the processed frequency domain data for the same frequency band at the same sampling point after the data combining operation of step 14.

For example, if the fundamental frequency of an audio signal is $F_5$, then the magnitudes of the frequency domain data of the fifth frequency band before step 13 and after step 14 are used as the basis for computing the scaling factors for the different sampling points. The processed frequency domain data for all frequency bands are then multiplied by the computed scaling factors for the respective sampling points.

2) The Second Modification:

In order to simulate the number of channels used in commercially available cochlear implant systems, as well as the limited number of channel electrodes to be implanted, the second modification involves frequency band integration techniques. In this embodiment, the scaling factor for a specific sampling point is obtained in the following manner:

Sub-step (a): All twenty-two channels are integrated before the sequence processing operation of step 13. That is, all input frequency domain data for all frequency bands in each channel are summed and subsequently averaged.

Figure 14:
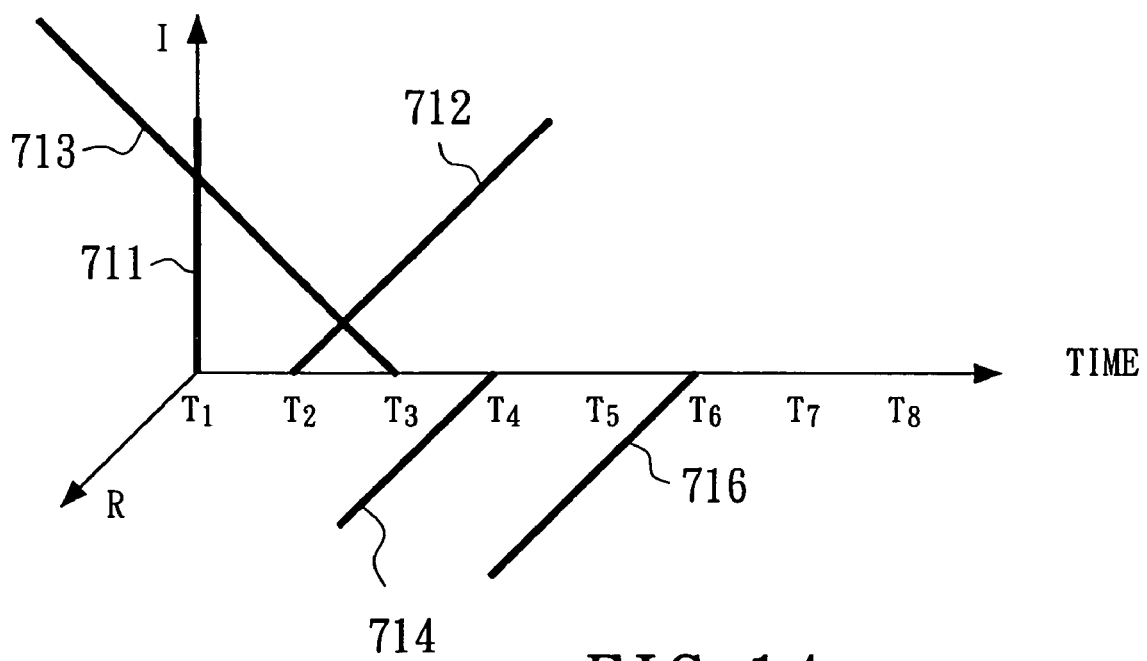
FIG. 14 illustrates composite channel data for a twenty-second channel.
Figure 15:
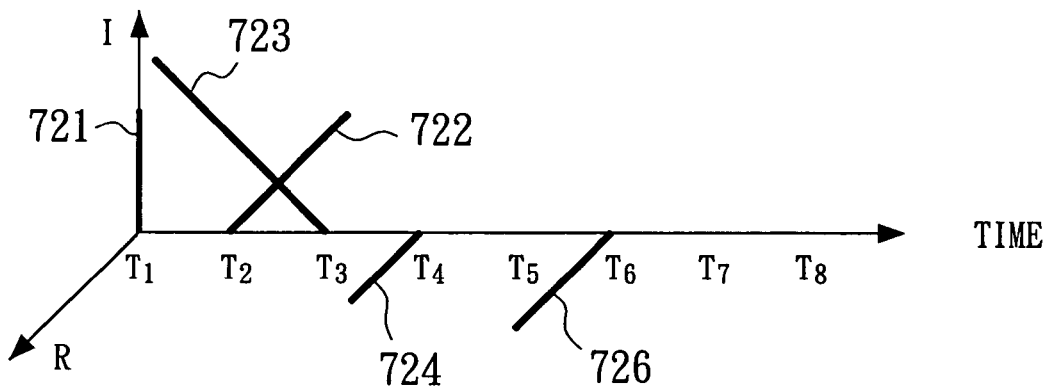
FIG. 15 illustrates averaged frequency-band data within the twenty-second channel.

Assuming that the aforesaid $22^{nd}$ channel only includes the first frequency band (represented by the first data set 30 of FIG. 5A) and the second frequency band (represented by the second data set 40 of FIG. 5B), summation of these two frequency bands will result in the channel-integrated data 711-714 and 716 shown in FIG. 14. The magnitudes of the channel-integrated data are divided by the number of the frequency bands in the $22^{nd}$ channel to result in the averaged frequency-band data 721-724 and 726 shown in FIG. 15. Hence, assuming that the distributions of the first and second data sets 30, 40 are the same, the averaged frequency-band data 721-724 and 726 in FIG. 15 will be the same as the input frequency domain data of the first and second data sets 30, 40 shown in FIGS. 5A and 5B.

At any sampling point, there are twenty-two sets of channel-integrated data, one of the data sets being illustrated in FIG. 14.

Sub-step (b): For a specific sampling point, the largest magnitude of the twenty-two sets of channel-integrated data is determined.

Figure 16A:
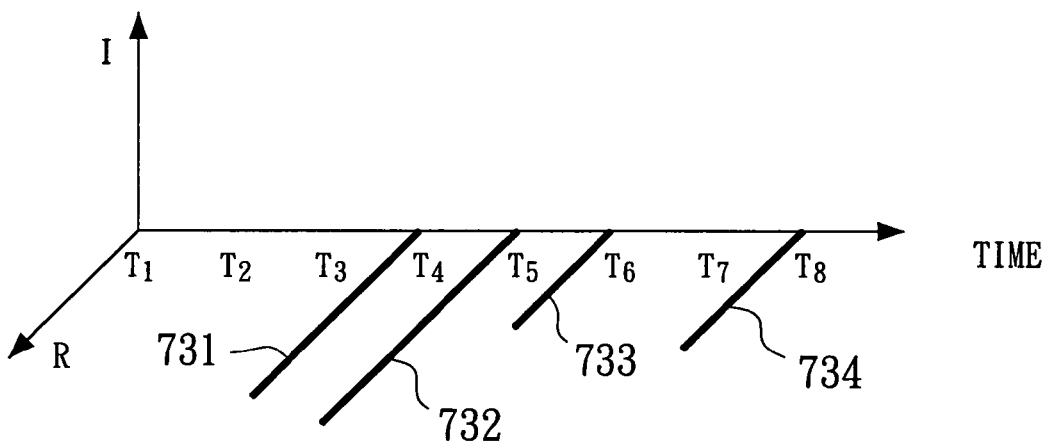
FIG. 16A illustrates distribution of frequency domain data of a frequency band ($F_1$) corresponding to the data of FIG. 15 after rearranging and combining operations.
Figure 16B:
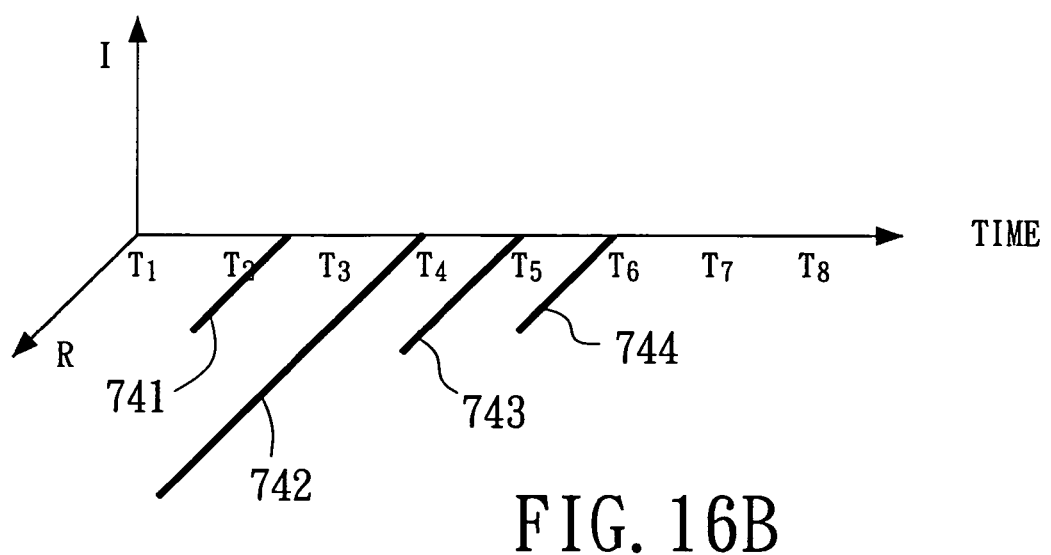
FIG. 16B illustrates distribution of frequency domain data of a frequency band ($F_2$) corresponding to the data of FIG. 15 after rearranging and combining operations.

Sub-step (c): The input frequency domain data of all frequency bands undergo the aforementioned sequence processing operation of step 13 and the aforementioned data combining operation of step 14. For example, the input frequency domain data corresponding to the frequency ($F_1$) become the processed frequency domain data 731-734 shown in FIG. 16A after the operations of steps 13 and 14. The input frequency domain data corresponding to the frequency ($F_2$) become the processed frequency domain data 741-744 shown in FIG. 16B after the operations of steps 13 and 14.

Sub-step (d): All twenty-two channels are integrated for the second time. That is, all processed frequency domain data for all frequency bands in each channel are summed to result in twenty-two sets of channel output data for each sampling point. The magnitudes of the channel output data are then divided by the number of the frequency bands in the respective channel to result in averaged frequency-band output data for the respective frequency band. The averaged frequency-band output data may be used for experimental signal recovery via inverse transformation techniques.

Sub-step (e): For a specific sampling point, the largest magnitude of the twenty-two sets of channel output data is determined.

Sub-step (f): Thereafter, the scaling factors at the specified sampling points are determined by dividing the largest magnitude found in sub-step (b) by the largest magnitude found in sub-step (e). Finally, the averaged frequency-band output data of all 256 frequency bands at each specified sampling point are then multiplied by the scaling factor corresponding to the specified sampling point.

It is worth noting that the result of sub-step (f) is the same as that obtained by magnitude scaling of all of the frequency bands in the same channel at the specified sampling point. Hence, in practice, it is feasible to scale the magnitudes of the twenty-two channel output signals directly by the scaling factor at the specified sampling point, and then output the scaled result to the corresponding channel electrode.

Since the frequency correspondence in the cochlea is a non-linear system, and in view of limitations in the number of channel electrodes that can be implanted in conventional cochlear implant systems, it is not possible for the channel electrodes to have a one-to-one correspondence relation with the frequency bands. As such, in the aforesaid second modification, processing is conducted in channel units, and average input frequency domain data and average processed frequency domain data for each frequency band of each channel are computed, which can lead to errors during signal recovery by inverse transformation. Note that in the aforesaid second modification, it is possible to modify Sub-step (a) by simply performing channel integration without magnitude averaging. In the future, if the number of channel electrodes can be increased such that the number of channels approximates the number of frequency bands, the aforesaid averaging operations may be dispensed with, and the result of the subsequent signal recovery operation by inverse transformation will most likely approach ideal expectations.

3) The Third Modification:

Operations similar to sub-steps (a), (c) and (d) of the aforesaid second alternative embodiment are likewise performed. However, instead of finding the largest magnitudes of channel data, the scaling factor is calculated as the quotient of the magnitude of the channel-integrated data for a specific channel at a certain sampling point and the magnitude of the channel output data for the same channel at the same sampling point.

For example, if the fundamental frequency of an audio signal is $F_5$, which belongs to the twenty-first channel, then the magnitudes of the channel-integrated data and the channel output data of the twenty-first channel are used as the basis for computing the scaling factors for the different sampling points. The frequency-band output data of all 256 frequency bands are then multiplied by the computed scaling factors for the respective sampling points.

Step 16—Electrode Transmission

According to their representative frequency ranges and corresponding channels, the 256 frequency bands processed in step 15 are further processed by electromagnetic conversion, and after parameter adjustment and encoding with reference to mapping data, the corresponding channel electrodes are located for simultaneous output. The mapping data are designed beforehand in accordance patients' clinical responses after the cochlear implant surgeries.

It is worth noting that, if the data combining operation of step 14 and the magnitude scaling operation of step 15 are omitted, the magnitude and phase values of each input frequency domain data and/or components thereof at the specified sampling points must be computed prior to electromagnetic conversion and before outputting via the corresponding channels. Nevertheless, the technique for combining the input frequency domain data is essentially the same as the above-mentioned techniques of this invention.

In this embodiment, assuming that the frequency ranges of the first and second frequency bands (i.e., the first and second data sets 30, 40 of FIGS. 5A and 5B) belong to the lower-frequency twenty-second channel, the first and second frequency bands will be outputted to the channel electrode that was implanted proximate to the apex of the cochlea after the aforesaid transformation and adjustment operations. Each of the channel electrodes stimulates the cochlea by transmission similar to the transmission of sound to the normal human cochlea and at time points typical of delays of traveling waves of a basilar membrane of the human cochlear. The stimulus is then transmitted to the human brain through the auditory nerves. The human brain is able to make inverse transformation of all input frequency domain data received thereby to recover the original audio signal.

Figure 3B:
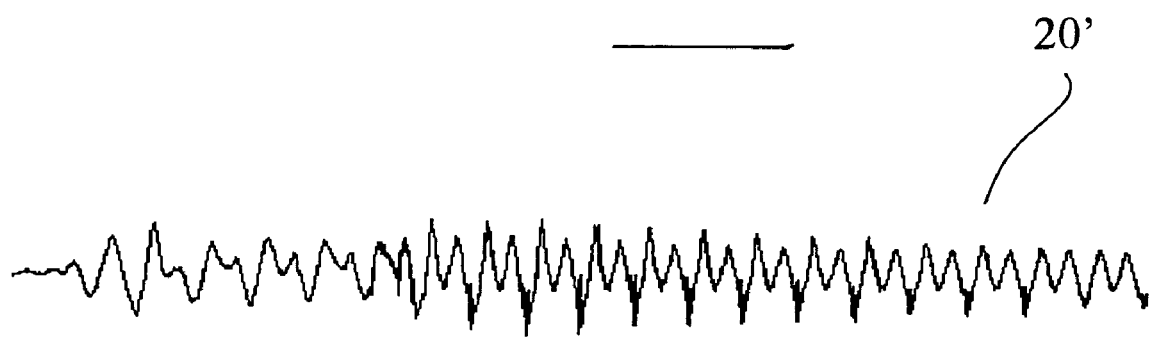
FIG. 3B illustrates an audio signal reconstructed from results of the signal processing method of the first preferred embodiment.

FIG. 3B illustrates a reconstructed audio signal 20' obtained by performing inverse Fast Fourier Transform (IFFT) upon the results of the method of the first preferred embodiment. The reconstructed audio signal 20' of FIG. 3B is shown to approximate the input audio signal 20 of FIG. 3A.

In sum, when the signal processing method of this invention is applied to a cochlear implant system, all features of the original audio signal, such as fundamental frequency, overtones, noise with stochastic resonance that enhances human hearing ("Human hearing enhanced by noise", Zeng F. G. et al., Brain Research. 869(1-2):251-5, 2000), etc., are maintained as much as possible. When compared with conventional signal processing methods that discard all signals having non-zero phases or that treat all signals as having a uniform zero phase, this invention permits transmission of phase characteristics at various frequencies so that more accurate audio data are transmitted to corresponding channel electrodes of the cochlear implant system.

Figure 17:
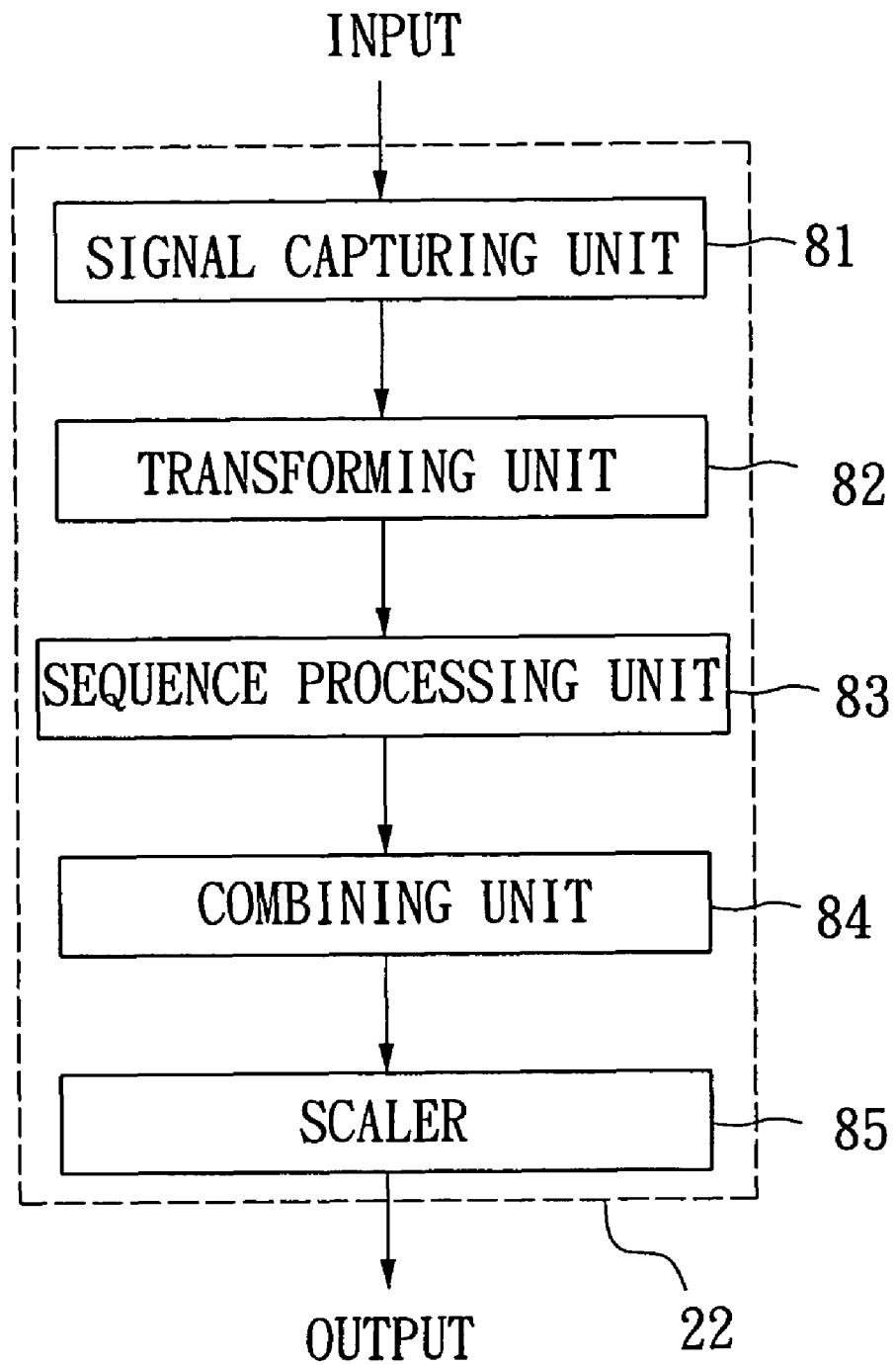
FIG. 17 is a block diagram of the preferred embodiment of a signal processing module according to the present invention.

Referring to FIGS. 1A, 2 and 17, the preferred embodiment of a signal processing module 22 for the cochlear implant system 2 is shown to include a signal capturing unit 81 responsible for the signal capturing operation of step 11, a transforming unit 82 coupled to the signal capturing unit 81 and responsible for the frequency transformation processing of step 12, a sequence processing unit 83 coupled to the transforming unit 82 and responsible for the sequence processing operation of step 13, a combining unit 84 coupled to the sequence processing unit 83 and responsible for the data combining operation of step 14, and a scaler 85 coupled to the combining unit 84 and responsible for executing the magnitude scaling operation of step 15.

Figure 18:
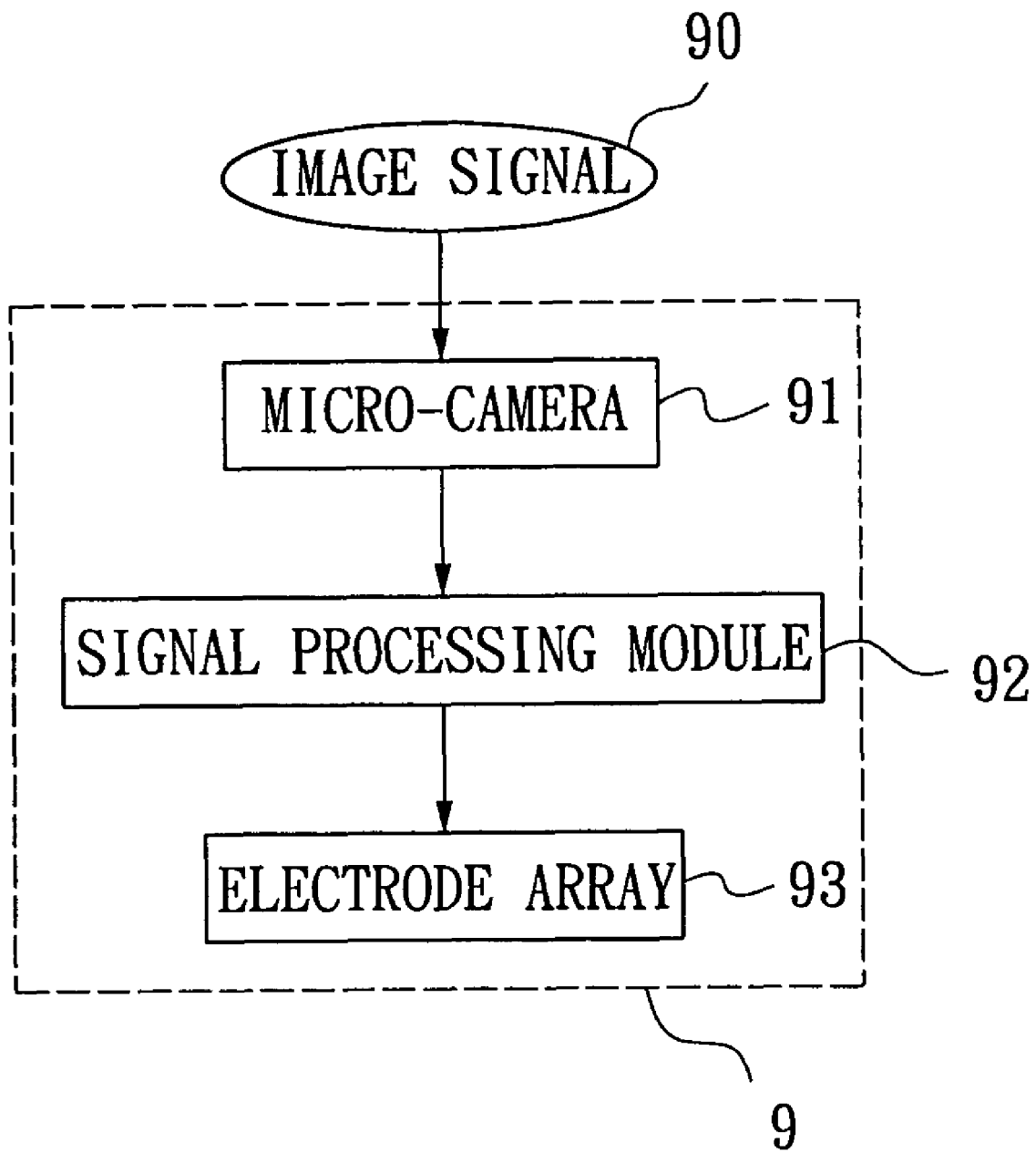
FIG. 18 is a simplified block diagram of a retinal implant system that employs the second preferred embodiment of a signal processing method according to this invention.

Referring to FIG. 18, a retinal implant system 9 that employs the second preferred embodiment of a signal processing method according to the present invention is shown to include a micro-camera 91 for picking up an image signal 90, a signal processing module 92 coupled to the micro-camera 91 for processing the image signal 90, and an electrode array 93 coupled to the signal processing module 92 and adapted to stimulate the retina. The micro-camera 91 may be mounted externally of the eyes (for example, on eyeglasses) or on the anterior retinal surface. In practice, instead of being implanted into the retina, the electrode array 93 may be implanted in the visual nerves or visual cortex of the brain.

The micro-camera 91 captures an image that is digitally encoded by the signal processing module 92, and the encoded signals are subsequently transmitted to the electrode array 93. The electrode array 93 converts the digital signals into electrical waves to directly stimulate retinal cells. The stimulus passes through visual nerves to the visual cortex of the brain such that a blind patient is able to recover his vision.

When the signal processing method of this invention is employed in a retinal implant device, the same steps 11-16 of the method of the first preferred embodiment are executed. The main differences reside in that the contents to be processed are those of a two-dimensional image signal instead of an input audio stream, and that the variable axis is a spatial axis instead of a time axis.

In this embodiment, an image consisting of 1000×1000 pixels is used as an illustrative example. The pixels are arranged in 1000 rows so that each row has 1000 points. Assuming that each point undergoes FFT with a sampling number of 256, 256 spatial frequency bands are obtained. Each spatial frequency band has 1000 input frequency domain data, that is, each row has 1000×256 sets of input frequency domain data.

Theoretically, the most ideal implementation of a retinal implant device is to implant each of 1000×1000×256 electrodes at a position in the retina that corresponds to a spatial frequency thereof. However, in view of inconclusive research pertinent to correspondence relationship between spatial frequencies to positions of the retina, visual nerves or visual cortex of the human brain, an electrode array 93 having 1000×1000×1 electrodes is used solely for illustration. Each electrode that is implanted into a specific position of the retina has a corresponding spatial frequency range, and receives at least one frequency band.

In accordance with the signal processing method of this invention, the input frequency domain data of each frequency band are processed by sequence processing on the spatial axis, summation of processed frequency domain data of all frequency bands that correspond to a common electrode at a common spatial point, and conversion into electrode output signals through mapping data tables and magnitude versus electromagnetic wave strength. The brain performs IFFT-like operations on the processed frequency domain data at various spatial frequencies in accordance with each spatial point (i.e., spatial position of each pixel) of the spatial axis so as to recover the phase and magnitude characteristics of the original image signal.

Preferably, in step 12, based on previous research, since spatial frequencies corresponding to human vision have a linear distribution, the image signal is processed using a window function prior to each FFT operation for increased concentration and accuracy.

This invention is further applicable to the processing of dynamic images in a retinal implant device. In the processing of dynamic images, by treating images in units of a time frame, the values of phase and magnitude of input frequency domain data at a specified spatial position of a pixel change with time. For instance, sixty frames are generated per second (that is, a 60 Hz sampling rate) for dynamic images. In this sense, since input frequency domain data at a specified spatial position of a pixel may be expressed on a time axis, frequency band adjustment on a time axis according to the method of this invention is thus applicable when processing dynamic images.

The third preferred embodiment of this invention is applied to an orthogonal frequency division multiplexing (OFDM) modulation system and to other systems that involve data transmission using various phases so that signal phase characteristics may be integrated and compressed to contain more information and to increase the transmission efficiency.

Figure 19:
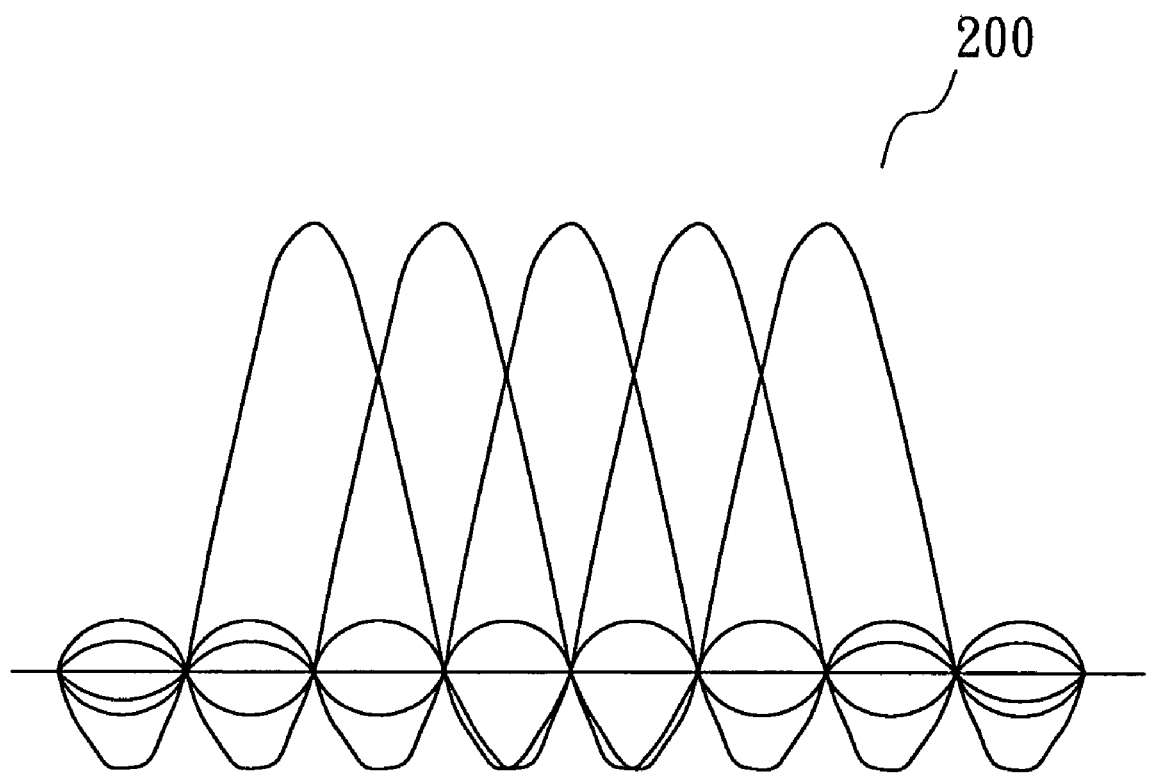
FIG. 19 is a frequency spectrum generated by an orthogonal frequency division multiplexing (OFDM) modulation system that employs the third preferred embodiment of a signal processing method according to the present invention.
Figure 20A:
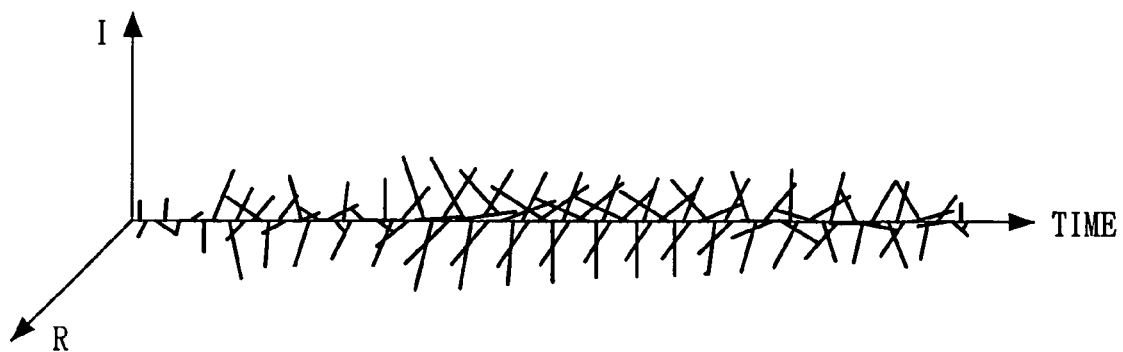
FIGS. 20A to 20D illustrate distribution of a first set of frequency domain data to be processed using the signal processing method of the third preferred embodiment on respective time axes.
Figure 20B:
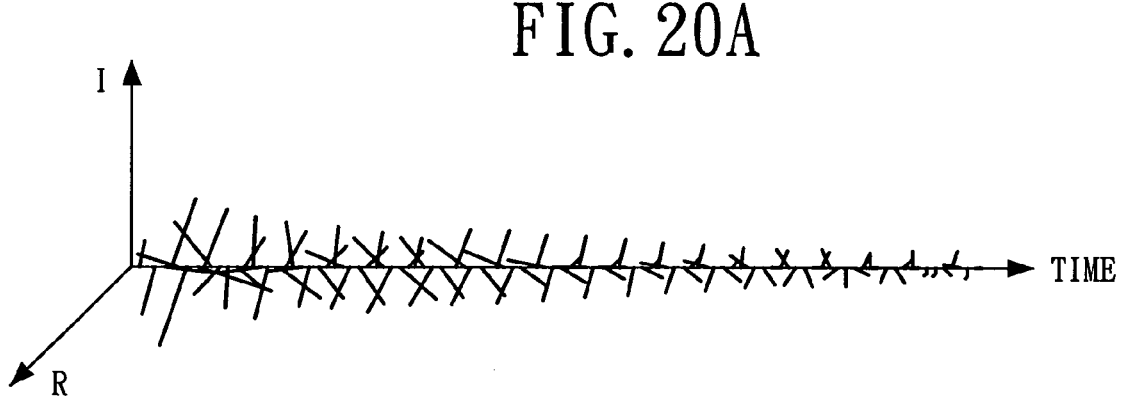
Figure 20C:
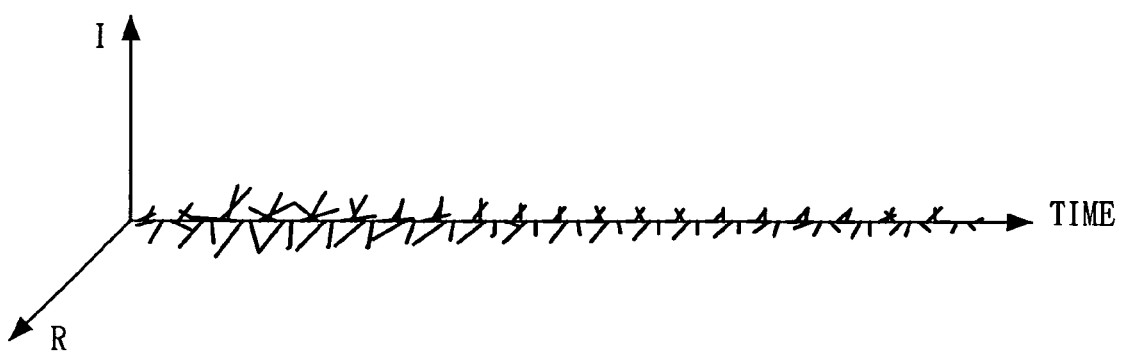
Figure 20D:
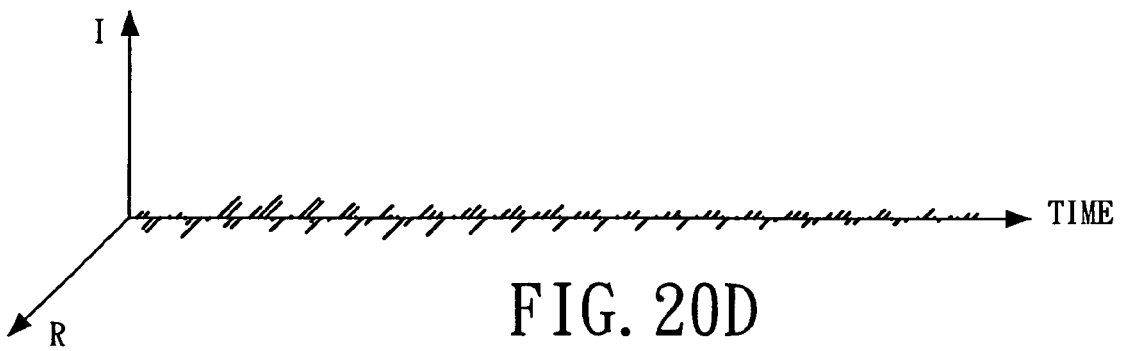
Figure 21A:
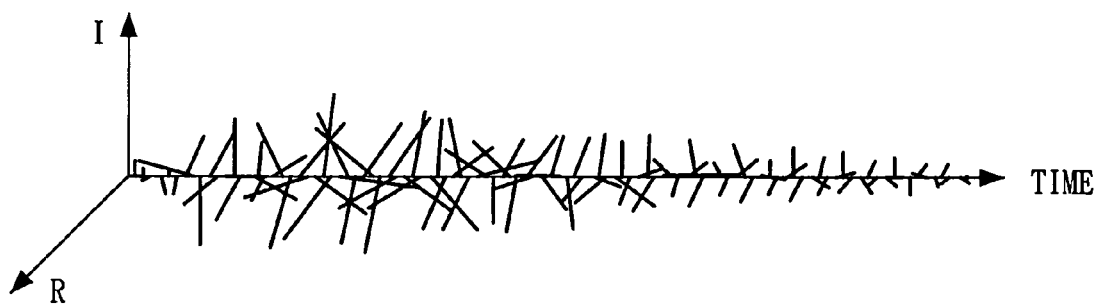
FIGS. 21A to 21D illustrate distribution of a second set of frequency domain data to be processed using the signal processing method of the third preferred embodiment on respective time axes.
Figure 21B:
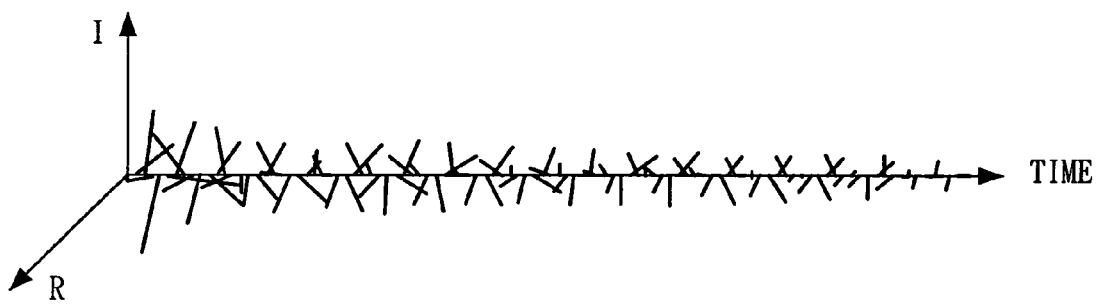
Figure 21C:
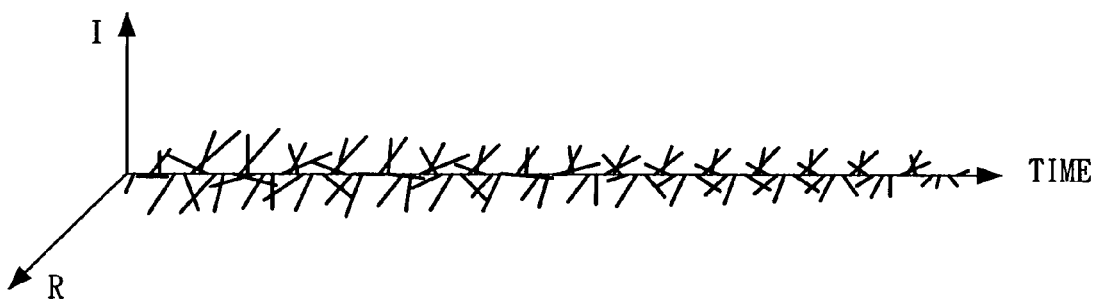
Figure 21D:
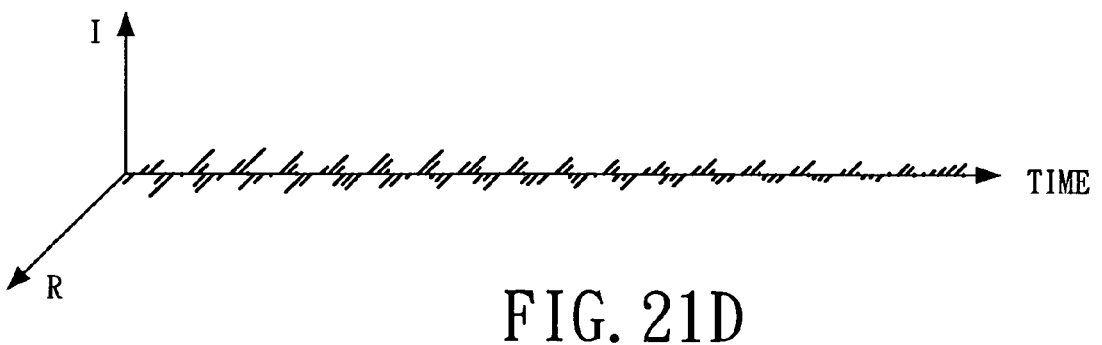
Figure 22A:
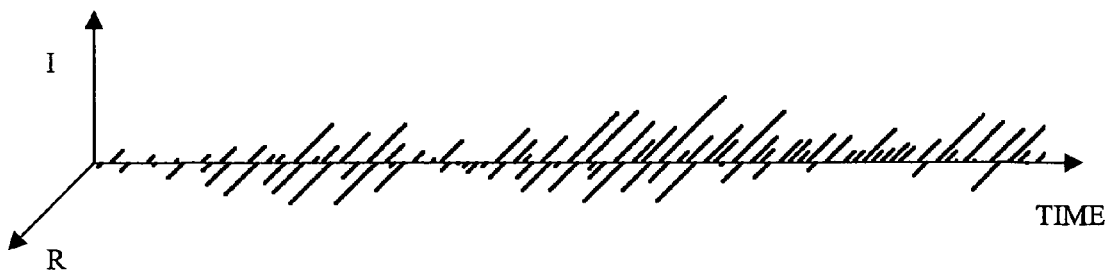
FIGS. 22A to 22D illustrate distribution of the frequency domain data of FIGS. 20A to 20D after rearranging and combining operations using reference phase angles of 0 and π.
Figure 22B:
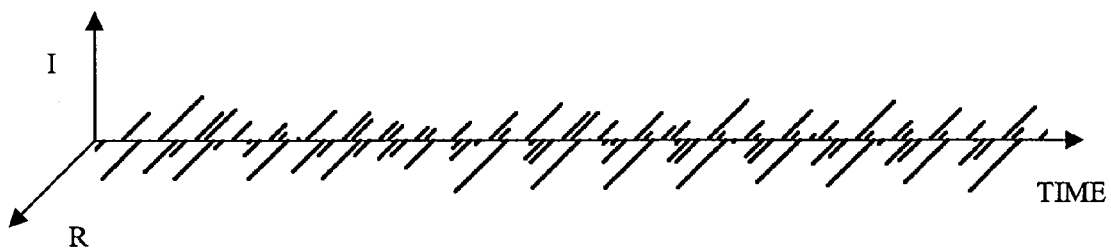
Figure 22C:
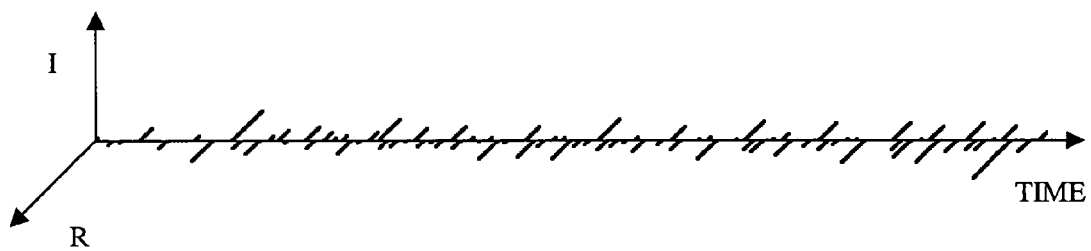
Figure 22D:
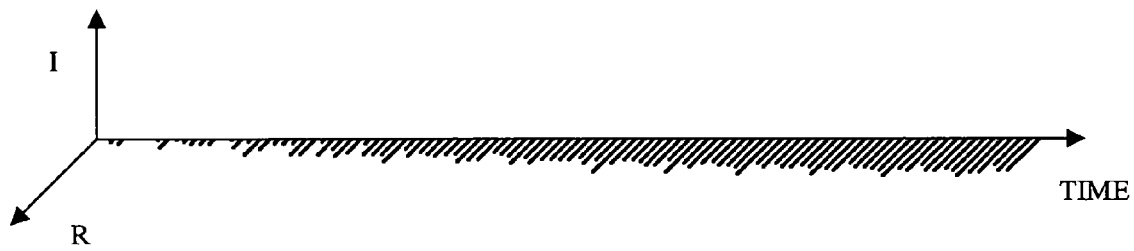
Figure 23A:
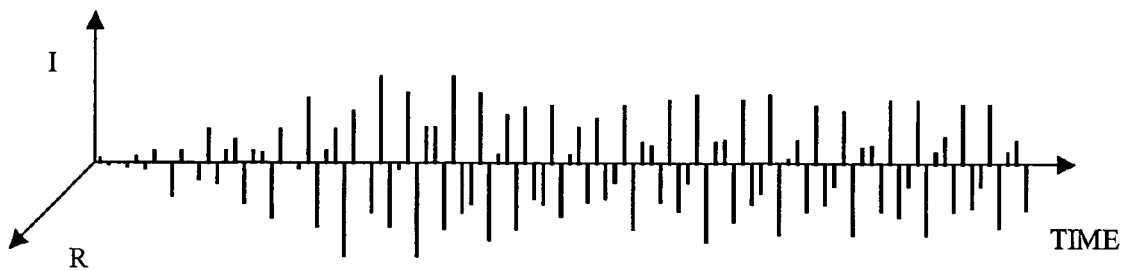
FIGS. 23A to 23D illustrate distribution of the frequency domain data of FIGS. 21A to 21D after rearranging and combining operations using reference phase angles of $0.5\pi$ and $1.5\pi$.
Figure 23B:
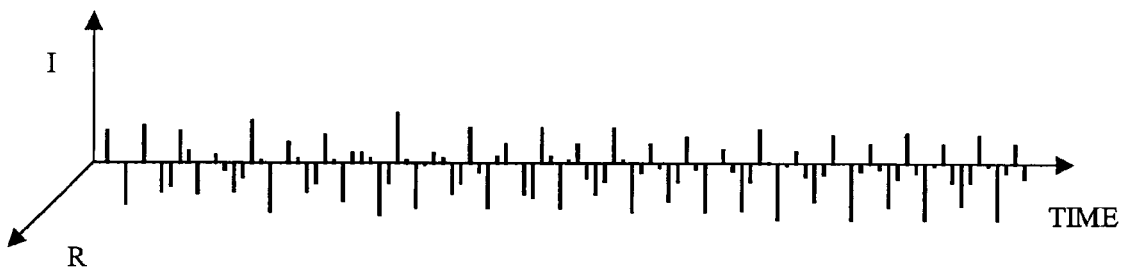
Figure 23C:
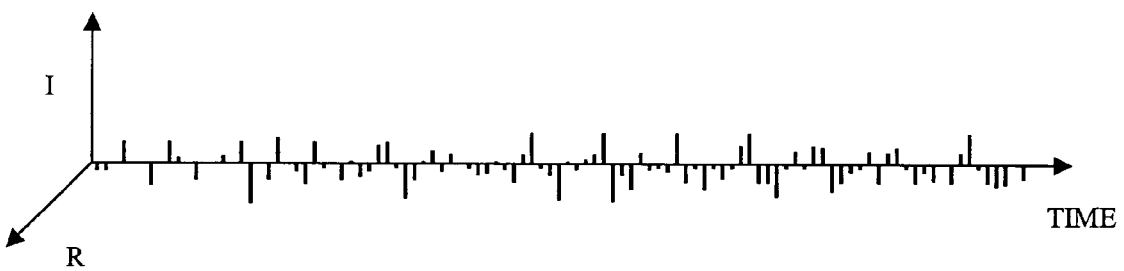
Figure 23D:
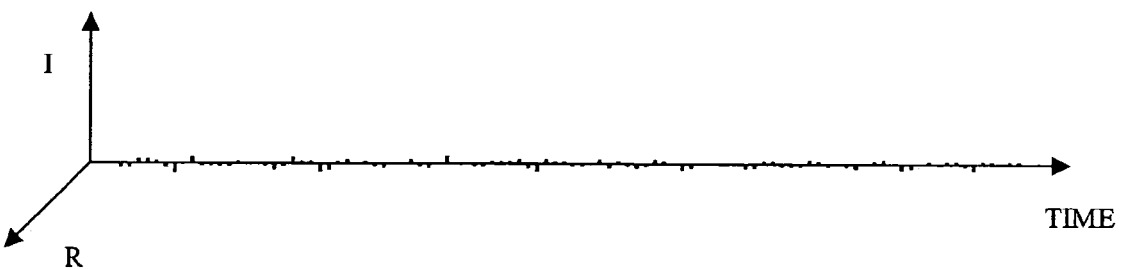

Referring to FIG. 19, an OFDM signal includes a plurality of sub-carriers 200, each of which corresponds to a specific signal that was transformed using quadrature amplitude modulation (QAM) upon a data stream. Each sub-carrier exhibits a sinc function in the frequency domain and is orthogonal to the other sub-carriers. When a transmitting end conducts IFFT on the signals so as to generate an analog electromagnetic wave to be broadcast at higher frequencies, the receiving end is able to receive and conduct FFT on a received signal so as to recover the original signals.

When the signal processing method of this invention is applied to OFDM, in step 12 of the aforesaid first preferred embodiment, the various signals are directly arranged on time axes of the frequency bands. Steps 13 and 14 of the aforesaid first preferred embodiment are then executed, wherein, in sub-step 131, the reference phase angles are a pair of $\pi$ out-of-phase angles.

Referring to FIGS. 20A, 20B, 20C and 20D, a plurality of signals of four sub-carriers form a first set of input frequency domain data on respective time axes, wherein the input frequency domain data at each sampling point has magnitude and phase characteristics. Referring to FIGS. 21A, 21B, 21C and 21D, a plurality of signals of four sub-carriers form a second set of input frequency domain data on respective time axes that are independent of the first set of input frequency domain data.

The first set of input frequency domain data that exhibit various magnitude and phase characteristics on the time axes in FIGS. 20A, 20B, 20C and 20D are processed using reference phase angles 0 and $\pi$ according to the signal processing method of the third preferred embodiment to result in the first set of processed frequency domain data shown in FIGS. 22A, 22B, 22C and 22D. As shown in FIGS. 22A to 22D, the processed frequency domain data all lie in the real number plane.

In the same manner, the second set of input frequency domain data that exhibit various magnitude and phase characteristics on the time axes in FIGS. 21A, 21B, 21C and 21D are processed using reference phase angles $0.5\pi$ and $1.5\pi$ according to the signal processing method of the third preferred embodiment to result in the second set of processed frequency domain data shown in FIGS. 23A, 23B, 23C and 23D. As shown in FIGS. 23A to 23D, the processed frequency domain data all lie in the imaginary number plane.

As such, through the method of this invention, OFDM data can be transformed to ones with fixed phases and subsequently combined with other data prior to transmission. In other words, the input frequency domain data (real numbers) of the frequency bands in FIGS. 22A to 22D may be combined with the input frequency domain data (imaginary numbers) of the frequency bands in FIGS. 23A to 23D to result in a new set of composite input frequency domain data for subsequent processing by IFFT and transmission using the original OFDM system.

On the other hand, the OFDM receiving end that embodies the signal processing method of this invention will conduct FFT upon the received signal so as to obtain a real number component thereof (i.e., the processed frequency domain data shown in FIGS. 22A, 22B, 22C and 22D) and an imaginary number component thereof (i.e., the processed frequency domain data shown in FIGS. 23A, 23B, 23C and 23D). The processed frequency domain data of the real and imaginary components are further subjected to IFFT, wherein the real number sequence is extracted and subjected to another FFT such that the input frequency domain data of FIGS. 20A, 20B, 20C and 20D are recovered from the processed frequency domain data of FIGS. 22A to 22D, and such that the input frequency domain data of FIGS. 21A, 21B, 21C and 21D are recovered from the processed frequency domain data of FIGS. 23A to 23D.

In sum, by applying the signal processing method of this invention in an OFDM system, an additional independent data set may be transmitted simultaneously, thereby realizing the effect of a double-speed ADSL, a double-speed wireless network card or double-speed digital audio-visual signal transmission.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A signal processing method for processing a plurality of input frequency domain data within a frequency band, each of the input frequency domain data having magnitude and phase characteristics and being associated with a phase parameter that corresponds to the phase characteristic thereof, said signal processing method comprising the steps of:
   a) arranging the input frequency domain data in sequence on a variable axis;
   b) rearranging, using a sequence processing unit, positions of the input frequency domain data on the variable axis, including calculating a displacement value ($\Delta T$) for at least one of the input frequency domain data with reference to at least the phase parameter thereof, and moving said at least one of the input frequency domain data from an initial position on the variable axis to an adjusted position on the variable axis with reference to the displacement value thus calculated; and
   c) combining the rearranged input frequency domain data that are disposed on the same position on the variable axis to result in a plurality of processed frequency domain data.

2. The signal processing method as claimed in claim 1, wherein, in step b), the displacement value ($\Delta T$) for said at least one of the input frequency domain data is calculated with reference to the phase parameter thereof and a frequency parameter that corresponds to a frequency characteristic of the frequency band.

3. The signal processing method as claimed in claim 2, wherein the frequency characteristic is the center frequency of the frequency band.

4. The signal processing method as claimed in claim 2, wherein step b) further includes calculating a phase difference ($\Delta\theta$) for said at least one of the input frequency domain data with reference to at least the phase parameter thereof, the displacement value ($\Delta T$) being calculated as a function of the phase difference ($\Delta\theta$) and the frequency parameter (T) according to the formula $$\Delta T = (\Delta\theta/2\Pi) \times (T).$$

5. The signal processing method as claimed in claim 4, wherein step b) further includes defining a reference phase angle, the phase difference ($\Delta\theta$) for said at least one of the input frequency domain data being calculated with reference to the phase parameter thereof and the reference phase angle.

6. The signal processing method as claimed in claim 5, wherein step b) further includes setting the phase characteristics of the rearranged input frequency domain data to correspond to the reference phase angle.

7. The signal processing method as claimed in claim 5, wherein, in step b), at least one of the input frequency domain data is decomposed into a first component lying on a plane corresponding to the reference phase angle, and a second component perpendicular to the first component, the displacement values being calculated for the first and second components of said at least one of the input frequency domain data.

8. The signal processing method as claimed in claim 4, wherein, in step b), when one of the input frequency domain data is capable of being decomposed to result in a component parallel to the variable axis, the component is added into the formula to result in a modified displacement value for said one of the input frequency domain data.

9. The signal processing method as claimed in claim 1, wherein, in step b), the variable axis has a plurality of output points, and said at least one of the input frequency domain data is moved from the initial position on the variable axis to an appropriate one of the output points on the variable axis with reference to the displacement value thus calculated.

10. The signal processing method as claimed in claim 1, wherein, in step b), at least one of the input frequency domain data on the variable axis has an initial position that is adjusted with reference to the phase parameter and a predefined frequency parameter.

11. The signal processing method as claimed in claim 1, wherein, in step c), the rearranged input frequency domain data are combined by vector summation.

12. The signal processing method as claimed in claim 1, further comprising the step:
   d) scaling the processed frequency domain data to limit the magnitudes thereof.

13. The signal processing method as claimed in claim 1, wherein the input frequency domain data are generated from an input audio stream, and the variable axis is a time axis.

14. The signal processing method as claimed in claim 1, wherein the input frequency domain data are generated from a two-dimensional image, and the variable axis is a spatial axis.

15. The signal processing method as claimed in claim 1, wherein step b) further includes calculating a phase difference ($\Delta\theta$) for said at least one of the input frequency domain data with reference to at least the phase parameter thereof, the displacement value ($\Delta T$) being calculated as a function of the phase difference ($\Delta\theta$) and a predefined frequency parameter (T) according to the formula $$\Delta T = (\Delta\theta/2\Pi) \times (T).$$

16. The signal processing method as claimed in claim 15, wherein step b) further includes defining a reference phase angle, the phase difference ($\Delta\theta$) for said at least one of the input frequency domain data being calculated with reference to the phase parameter thereof and the reference phase angle.

17. The signal processing method as claimed in claim 16, wherein step b) further includes setting the phase characteristics of the rearranged input frequency domain data to correspond to the reference phase angle.

18. A signal processing module for processing a plurality of input frequency domain data within a frequency band, each of the input frequency domain data having magnitude and phase characteristics and being associated with a phase parameter that corresponds to the phase characteristic thereof, said signal processing module comprising:
   a transforming unit for arranging the input frequency domain data in sequence on a variable axis;
   a sequence processing unit, coupled to said transforming unit, for rearranging positions of the input frequency domain data on the variable axis; and a combining unit, coupled to said sequence processing unit, for combining the rearranged input frequency domain data that are disposed on the same position on the variable axis to result in a plurality of processed frequency domain data;

wherein said sequence processing unit calculates a displacement value ($\Delta T$) for at least one of the input frequency domain data with reference to at least the phase parameter thereof, and moves said at least one of the input frequency domain data from an initial position on the variable axis to an adjusted position on the variable axis with reference to the displacement value thus calculated.

19. The signal processing module as claimed in claim 18, wherein said sequence processing unit calculates the displacement value ($\Delta T$) for said at least one of the input frequency domain data with reference to the phase parameter thereof and a frequency parameter that corresponds to a frequency characteristic of the frequency band.

20. The signal processing module as claimed in claim 19, wherein the frequency characteristic is the center frequency of the frequency band.

21. The signal processing module as claimed in claim 19, wherein said sequence processing unit further calculates a phase difference ($\Delta\theta$) for said at least one of the input frequency domain data with reference to at least the phase parameter thereof, and calculates the displacement value ($\Delta T$) as a function of the phase difference ($\Delta\theta$) and the frequency parameter (T) according to the formula $$\Delta T = (\Delta\theta/2\Pi) \times (T).$$

22. The signal processing module as claimed in claim 21, wherein said sequence processing unit further defines a reference phase angle, and calculates the phase difference ($\Delta\theta$) for said at least one of the input frequency domain data with reference to the phase parameter thereof and the reference phase angle.

23. The signal processing module as claimed in claim 22, wherein said sequence processing unit further sets the phase characteristics of the rearranged input frequency domain data to correspond to the reference phase angle.

24. The signal processing module as claimed in claim 22, wherein at least one of the input frequency domain data is decomposed by said sequence processing unit into a first component lying on a plane corresponding to the reference phase angle, and a second component perpendicular to the first component, said sequence processing unit calculating the displacement values for the first and second components of said at least one of the input frequency domain data.

25. The signal processing module as claimed in claim 21, wherein, when one of the input frequency domain data is capable of being decomposed to result in a component parallel to the variable axis, said sequence processing unit adds the component into the formula to result in a modified displacement value for said one of the input frequency domain data.

26. The signal processing module as claimed in claim 18, wherein the variable axis has a plurality of output points, and said at least one of the input frequency domain data is moved by said sequence processing unit from the initial position on the variable axis to an appropriate one of the output points on the variable axis with reference to the displacement value calculated by said sequence processing unit.

27. The signal processing module as claimed in claim 18, wherein at least one of the input frequency domain data on the variable axis has an initial position that is adjusted by said sequence processing unit with reference to the phase parameter and a predefined frequency parameter.

28. The signal processing module as claimed in claim 18, wherein said combining unit combines the rearranged input frequency domain data by vector summation.

29. The signal processing module as claimed in claim 18, further comprising a scaler, coupled to said combining unit, for scaling the processed frequency domain data to limit the magnitudes thereof.

30. The signal processing module as claimed in claim 18, wherein the input frequency domain data are generated from an input audio stream, and the variable axis is a time axis.

31. The signal processing module as claimed in claim 18, wherein the input frequency domain data are generated from a two-dimensional image, and the variable axis is a spatial axis.

32. The signal processing module as claimed in claim 18, wherein said sequence processing unit further calculates a phase difference ($\Delta\theta$) for said at least one of the input frequency domain data with reference to at least the phase parameter thereof, and calculates the displacement value ($\Delta T$) as a function of the phase difference ($\Delta\theta$) and a predefined frequency parameter (T) according to the formula $$\Delta T = (\Delta\theta/2\Pi) \times (T).$$

33. The signal processing module as claimed in claim 32, wherein said sequence processing unit further defines a reference phase angle, and calculates the phase difference ($\Delta\theta$) for said at least one of the input frequency domain data with reference to the phase parameter thereof and the reference phase angle.

34. The signal processing module as claimed in claim 33, wherein said sequence processing unit further sets the phase characteristics of the rearranged input frequency domain data to correspond to the reference phase angle.

* * * * *